(12) United States Patent
Yang et al.

(10) Patent No.: US 6,916,907 B1
(45) Date of Patent: Jul. 12, 2005

(54) NUCLEIC ACIDS ENCODING OSTEOPROTEGERN-LIKE PROTEINS AND METHODS OF USING SAME

(75) Inventors: Meijia Yang, East Lyme, CT (US); Henri Lichenstein, Madison, CT (US); William F. McDonald, Madison, CT (US); Richard A. Shimkets, West Haven, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/422,680

(22) Filed: Oct. 21, 1999

Related U.S. Application Data

(60) Provisional application No. 60/156,993, filed on Oct. 1, 1999, and provisional application No. 60/105,481, filed on Oct. 23, 1998.

(51) Int. Cl.[7] .......................... A61K 38/00; C07K 2/00; C07K 4/00; C07K 5/00; C07K 7/00
(52) U.S. Cl. .................... 530/350; 530/300; 514/1; 514/2; 514/12; 424/184.1; 424/185.1
(58) Field of Search ............................... 530/350, 300; 514/1, 2, 12; 424/184.1, 185.1

(56) References Cited

U.S. PATENT DOCUMENTS 6,013,476 A * 1/2000 Deen et al.

FOREIGN PATENT DOCUMENTS

| EP | 0861850 A1 | 9/1998 |
|---|---|---|
| EP | 0869179 A | 10/1998 |
| WO | WO 98/30694 | 7/1998 |
| WO | WO 98/56892 | 12/1998 |
| WO | WO 99/11790 | 3/1999 |
| WO | WO 99/15663 | 4/1999 |

OTHER PUBLICATIONS

Attached database sheet, amino acid sequence comparison U.S. patent No. 6,013,476.*
Attached database sheet, amino acid sequence comparison, Accession No. O75509/ AF068868.*
Attached database sheet, amino acid sequence comparison, Accession No. AAW75792/ EP 869179 A1.*
Antibodies: A Laboratory Manual, pp. 96–99, Cold Spring Harbor Laroratory, 1988.*
Lazar et al. Transforming Growth Factor alpha: Mutation of Aspartic acid 47 and Leucine 48 Results in Different Biological Activities, Molecular and Cellular Biology 8(3):1247–1252, Mar. 1988.*
Ashkenazi, A. and V. M. Dixit (1998). Death receptors: signaling and modulation. Science 281: 1305–1308.
Golstein, P. (1997). Cell death: TRAIL and its receptors. Curr Biol. 7: R750–753.
Pan, G., J. H. Bauer, et al. (1998). Identification and functional characterization of DR6, a novel death domain–containing TNF receptor. FEBS Lett 431: 351–356.
Simonet, W. S., D. L. Lacey, et al. (1997). Osteoprotegerin: a novel secreted protein involved in the regulation of bone density [see comments]. Cell 89: 309–319.
Simonet et al., "Osteoprotegerin: a novel secreted protein involved in the regulation of bone density" Cell 89:309–319, 1997.
Smith et al., "The TNF receptor superfamily of cellular and viral proteins: activation, costimulation and death" Cell 76:9590962, 1994.
Pan et al., "Homo sapiens TNFR–related death receptor–6 (DR–6) mRNA, complete cds", Database EMBL Online, Accession No. AF068868, Sep. 9, 1998.
NCI–CGAP, "Homo sapiens cDNA clone IMAGE 1609776", Database EMBL Online, Accession No. AA991608, Jun. 5, 1998.
NCI–CGAP, "Homo sapiens cDNA clone IMAGE 1369096", Database EMBL Online, Accession No. A837291, Feb. 27, 1998.
Hillier et al., "Homo sapiens cDNA clone IMAGE 280262", Database EMBL Online, Accession No. N49208, Feb. 18, 1996.
Marra et al., "Mus musculus cDNA clone IMAGE 533995", Database EMBL Online, Accession No. AA072902, Oct. 5, 1996.
International Search Report WO 99/24913 Aug. 24, 2000.

* cited by examiner

Primary Examiner—Alana M. Harris
(74) Attorney, Agent, or Firm—Ivor R. Elrifi, Esq.; Naomi S. Biswas, Esq.; Mintz, Levin, Cohn, Ferris Glovsky and Popeo, P.C.

(57) ABSTRACT

Disclosed are osteoprotegerin-like polypeptides, nucleic acids encoding osteoprotegerin-like polypeptides, and methods of using these molecules. The osteoprotegerin-like polypeptides sequence homology to osteoprotegerin and tumor necrosis factor receptor molecules.

4 Claims, 10 Drawing Sheets

```
  1
    GCGNCCGCGNNGNGNGCAAGGTGCTGAGCGCCCCTAGAGCCTCCCTTGCCGCCTCCCTCCTCTGCCCGGCCGCAGCAGTG
 81
    CACATGGGTGTTGGAGGTAGATGGGCTCCCGGCCGGGAGGCGGCGGTGGATGCGGCGCTGGGCAGAAGCAGCCGCCGAT
                                       MetGlySerArgProGlyGlyGlyGlyGlyCysGlyAlaGlyGlnLysGlnProProIl
161
    TCCAGCTGCCCCGCGCGCCCCGGCCACCTTGCGAGTCCCCGGTTCAGCCATGGGGACCTCTCCGAGCAGCAGCACCGCCC
    eProAlaAlaProArgAlaProAlaThrLeuArgValProGlySerAlaMetGlyThrSerProSerSerSerThrAlaL
                                 *
241
    TCGCCTCCTGCAGCAGCATCGCCCGCCGAGCCACAGCCACGATGATCGCGGGCTCCCTTCTCCTGCTTGGATTCCTTAGC
    euAlaSerCysSerSerIleAlaArgArgAlaThrAlaThrMetIleAlaGlySerLeuLeuLeuLeuGlyPheLeuSer
321
    ACCACCACAGCTCAGCCAGAACAGAAGGCCTCGAATCTCATTGGCACATACCGCCATGTTGACCGTGCCACCGGCCAGGT
    ThrThrThrAlaGlnProGluGlnLysAlaSerAsnLeuIleGlyThrTyrArgHisValAspArgAlaThrGlyGlnVa
401
    GCTCAACTGTGACAAGTGTCCAGCAGGAACCTATGTCTCTGAGCATTGTACCAACACAAGCCTGCGCGTCTGCAGCAGTT
    lLeuAsnCysAspLysCysProAlaGlyThrTyrValSerGluHisCysThrAsnThrSerLeuArgValCysSerSerC
481
    GCCCTGTGGGGACCTTTACCAGGCATGAGAATGGCATAGAGAAATGCCATGACTGTAGTCAGCCATGCCCATGGCCAATG
    ysProValGlyThrPheThrArgHisGluAsnGlyIleGluLysCysHisAspCysSerGlnProCysProTrpProMet
561
    ATTGAGAAATTACCTTGTGCTGCCTTGACTGACCGAGAATGCACTTGCCCACCTGGCATGTTCCAGTCTAACGCTACCTG
    IleGluLysLeuProCysAlaAlaLeuThrAspArgGluCysThrCysProProGlyMetPheGlnSerAsnAlaThrCy
641
    TGCCCCCCATACGGTGTGTCCTGTGGGTTGGGGTGTGCGGAAGAAAGGGACAGAGACTGAGGATGTGCGGTGTAAGCAGT
    sAlaProHisThrValCysProValGlyTrpGlyValArgLysLysGlyThrGluThrGluAspValArgCysLysGlnC
721
    GTGCTCGGGGTACCTTCTCAGATGTGCCTTCTAGTGTGATGAAATGCAAAGCATACACAGACTGTCTGAGTCAGAACCTG
    ysAlaArgGlyThrPheSerAspValProSerSerValMetLysCysLysAlaTyrThrAspCysLeuSerGlnAsnLeu
801
    GTGGTGATCAAGCCGGGGACCAAGGAGACAGACAACGTCTGTGGCACACTCCCGTCCTTCTCCAGCTCCACCTCACCTTC
    ValValIleLysProGlyThrLysGluThrAspAsnValCysGlyThrLeuProSerPheSerSerSerThrSerProSe
881
    CCCTGGCACAGCCATCTTTCCACGCCCTGAGCACATGGAAACCCATGAAGTCCCTTCCTCCACTTATGTTCCCAAAGGTA
    rProGlyThrAlaIlePheProArgProGluHisMetGluThrHisGluValProSerSerThrTyrValProLysGlyA
961
    ACTTAACCTCATGAATTATTTATTTGAGGAAGGCTTTGAGCCCAGTGGAGGTACCAAGAGTGGGCTTATACCAAAGATGT
    snLeuThrSer
1041
    TTTCTCCATTTCGTGTATTCCAAAGTCACCCCTTGGAGAGAGGCCTTCATATGGTGGCTAATTAAATCTGGCTTTTTTGG
1121
    ACTTAATAGAAACATGTAGACTCAGAATTTTTCTGTTAGGGGAGATCAGATATCTAAAAACTAGGTCACATCAAGCTATA
1201
    AAATATGAACCAAGAGAAACAAGGACAGCGTGTGACCTTATGTAAGTTACTTAACCTCTTCAGGCCTCAGTTTCAAACTT
1281
    GTCAAACAAATGAATAATTTAGATGTTTAAGGTTCCTTCCAGATCAAAAGTTTTCCAACATGGAGTCAGTCCCAGGTAGA
1361
    CATAGCCAGGAGCAGAGAAGAGGGAGAAAGGAAGAAAATACCATTACATCCGGAAGCGAGAGATGAATTTTGAATCCAGG
1441
    TGGGGCAAAGAATGGGTAGGAAAGTTAGAAGCTCAGGAAATAAGCAAATTTGTATCAGATTGAAGGTAACTAGCACTCAT
1521
    GTCTGGAAAATAATAACTTTATTTTTTCCAAATGATTTTAACTTTACTCCTTATATCAATTATTCAAGTTTTCCATCAGA
1601
    ACCTCAAGCAGAATATAAAATTTATCCTTTATTTTCAAATCCTTTTTGATTTAATGTAATTTTCATGAGATGATGACCAA
1681
    CTTGAG
```

Fig. 1

1
GCGNCCGCGNNGNGNGCAAGGTGCTGAGCGCCCCTAGNGCCTCCCTTGCCGCCTCCCTCCTCTGCCCGGCCGTAGCAGTG
81
CACATGGGGTGTTGGAGGTAGATGGGCTCCCGGCCGGGAGGCGGCGGTGGATGCGGCGCTGGGCAGAAGCAGCCGCCGAT
            MetGlySerArgProGlyGlyGlyGlyCysGlyAlaGlyGlnLysGlnProProIl
161
TCCAGCTGCCCCGCGCGCCCCGGGCACCTTGCGAGTCCCCGGTTCAGCCATGGGGACCTCTCCGAGCAGCAGCACCGCCC
eProAlaAlaProArgAlaProGlyThrLeuArgValProGlySerAlaMetGlyThrSerProSerSerSerThrAlaL
241
TCGCCTCCTGCAGCCGCATCGCCCGCCGAGCCACAGCCACGATGATCGCGGGCTCCCTTCTCCTGCTTGGATTCCTTAGC
euAlaSerCysSerArgIleAlaArgArgAlaThrAlaThrMetIleAlaGlySerLeuLeuLeuLeuGlyPheLeuSer
321
ACCACCACAGCTCAGCCAGAACAGAAGGCCTCGAATCTCATTGGCACATACCGCCATGTTGACCGTGCCACCGGCCAGGT
ThrThrThrAlaGlnProGluGlnLysAlaSerAsnLeuIleGlyThrTyrArgHisValAspArgAlaThrGlyGlnVa
401
GCTAACCTGTGACAAGTGTCCAGCAGGAACCTATGTCTCTGAGCATTGTACCAACACAAGCCTGCGCGTCTGCAGCAGTT
lLeuThrCysAspLysCysProAlaGlyThrTyrValSerGluHisCysThrAsnThrSerLeuArgValCysSerSerC
481
GCCCTGTGGGGACCTTTACCAGGCATGAGAATGGCATAGAGAAATGCCATGACTGTAGTCAGCCATGCCCATGGCCAATG
ysProValGlyThrPheThrArgHisGluAsnGlyIleGluLysCysHisAspCysSerGlnProCysProTrpProMet
561
ATTGAGAAATTACCTTGTGCTGCCTTGACTGACCGAGAATGCACTTGCCCACCTGGCATGTTCCAGTCTAACGCTACCTG
IleGluLysLeuProCysAlaAlaLeuThrAspArgGluCysThrCysProProGlyMetPheGlnSerAsnAlaThrCy
641
TGCCCCCCACATACGGTGTGTCCTGTGGGTTGGGGTGTGCGGAAGAAAGGGACAGAGACTGAGGATGTGCGGTGTAAGCAGT
sAlaProHisThrValCysProValGlyTrpGlyValArgLysLysGlyThrGluThrGluAspValArgCysLysGlnC
721
GTGCTCGGGGTACCTTCTCAGATGTGCCTTCTAGTGTGATGAAATGCAAAGCATACACAGACTGTCTGAGTCAGAACCTG
ysAlaArgGlyThrPheSerAspValProSerSerValMetLysCysLysAlaTyrThrAspCysLeuSerGlnAsnLeu
801
GTGGTGATCAAGCCGGGGACCAAGGAGACAGACAACGTCTGTGGCACACTCCCGTCCTTCTCCAGCTCCACCTCACCTTC
ValValIleLysProGlyThrLysGluThrAspAsnValCysGlyThrLeuProSerPheSerSerSerThrSerProSe
881
CCCTGGCACAGCCATCTTTCCACGCCCTGAGCACATGGAAACCCATGAAGTCCCTTCCTCCACTTATGTTCCCAAAGGCA
rProGlyThrAlaIlePheProArgProGluHisMetGluThrHisGluValProSerSerThrTyrValProLysGlyM
961
TGAACTCAACAGAATCCAACTCTTCTGCCTCTGTTAGACCAAAGGTACTGAGTAGCATCCAGGAAGGGACAGTCCCTGAC
etAsnSerThrGluSerAsnSerSerAlaSerValArgProLysValLeuSerSerIleGlnGluGlyThrValProAsp
1041
AACACAAGCTCAGCAAGGGGGAAGGAAGACGTGAACAAGACCCTCCCAAACCTTCAGGTAGTCAACCACCAGCAAGGCCC
AsnThrSerSerAlaArgGlyLysGluAspValAsnLysThrLeuProAsnLeuGlnValValAsnHisGlnGlnGlyPr
1121
CCACCACAGACACATCCTGAAGCTGCTGCCGTCCATGGAGGCCACTGGGGGCGAGAAGTCCAGCACGCCCATCAAGGGCC
oHisHisArgHisIleLeuLysLeuLeuProSerMetGluAlaThrGlyGlyGluLysSerSerThrProIleLysGlyP
1201
CCAAGAGGGGACATCCTAGACAGAACCTACACAAGCATTTTGACATCAATGAGCATTTGCCCTGGATGATTGTGCTTTTC
roLysArgGlyHisProArgGlnAsnLeuHisLysHisPheAspIleAsnGluHisLeuProTrpMetIleValLeuPhe
1281
CTGCTGCTGGTGCTTGTGGTGATTGTGGTGTGCAGTATCCGGAAAAGCTCGAGGACTCTGAAAAAGGGGCCCCGGCAGGA
LeuLeuLeuValLeuValValIleValValCysSerIleArgLysSerSerArgThrLeuLysLysGlyProArgGlnAs
1361
TCCCAGTGCCATTGTGGAAAAGGCAGGGCTGAAGAAATCCATGACTCCAACCCAGAACCGGGAGAAATGGATCTACTACT
pProSerAlaIleValGluLysAlaGlyLeuLysLysSerMetThrProThrGlnAsnArgGluLysTrpIleTyrTyrC
1441
GCAATGGCCATGGTATCGATATCCTGAAGCTTGTAGCAGCCCAAGTGGGAAGCCAGTGGAAAGATATCTATCAGTTTCTT
ysAsnGlyHisGlyIleAspIleLeuLysLeuValAlaAlaGlnValGlySerGlnTrpLysAspIleTyrGlnPheLeu
1521
TGCAATGCCAGTGAGAGGGAGGTTGCTGCTTTCTCCAATGGGTACACAGCCGACCACGAGCGGGCCTACGCAGCTCTGCA
CysAsnAlaSerGluArgGluValAlaAlaPheSerAsnGlyTyrThrAlaAspHisGluArgAlaTyrAlaAlaLeuGl
1601
GCACTGGACCATCCGGGGCCCCGAGGCCAGCCTCGCCCAGCTAATTAGCGCCCTGCGCCAGCACCGGAGAAACGATGTTG
nHisTrpThrIleArgGlyProGluAlaSerLeuAlaGlnLeuIleSerAlaLeuArgGlnHisArgArgAsnAspValV
1681
TGGAGAAGATTCGTGGGCTGATGGAAGACACCACCCAGCTGGAAACTGACAAACTAGCTCTCCCGATGAGCCCCAGCCCG
alGluLysIleArgGlyLeuMetGluAspThrThrGlnLeuGluThrAspLysLeuAlaLeuProMetSerProSerPro

Fig. 2A

```
1761
    CTTAGCCCGAGCCCCATCCCCAGCCCCAACGCGAAACTTGAGAATTCCGCTCTCCTGACGGTGGAGCCTTCCCCACAGGA
    LeuSerProSerProIleProSerProAsnAlaLysLeuGluAsnSerAlaLeuLeuThrValGluProSerProGlnAs
1841
    CAAGAACAAGGGCTTCTTCGTGGATGAGTCGGAGCCCCTTCTCCGCTGTGACTCTACATCCAGCGGCTCCTCCGCGCTGA
    pLysAsnLysGlyPhePheValAspGluSerGluProLeuLeuArgCysAspSerThrSerSerGlySerSerAlaLeuS
1921
    GCAGGAACGGTTCCTTTATTACCAAAGAAAAGAAGGACACAGTGTTGCGGCAGGTACGCCTGGACCCCTGTGACTTGCAG
    erArgAsnGlySerPheIleThrLysGluLysLysAspThrValLeuArgGlnValArgLeuAspProCysAspLeuGln
2001
    CCTATCTTTGATGACATGCTCCACTTTCTAAATCCTGAGGAGCTGCGGGTGATTGAAGAGATTCCCCAGGCTGAGGACAA
    ProIlePheAspAspMetLeuHisPheLeuAsnProGluGluLeuArgValIleGluGluIleProGlnAlaGluAspLy
2081
    ACTAGACCGGCTATTCGAAATTATTGGAGTCAAGAGCCAGGAAGCCAGCCAGACCCTCCTGGACTCTGTTTATAGCCATC
    sLeuAspArgLeuPheGluIleIleGlyValLysSerGlnGluAlaSerGlnThrLeuLeuAspSerValTyrSerHisL
2161
    TTCCTGACCTGCTGTAGAACATTAGGGATACTGCATTCTGGAAATTACTCAATTTAGTGGCAGGGTGGTTTTTTANTTTT
    euProAspLeuLeu
2241
    CTTCTGTTTCTGATTTTTGTTGTTTGGGGTG
```

Fig. 2B

OSTEOPROTEGERIN - HOMO SAPIENS (HUMAN), 401 aa.

Length = 401

Score = 285 (100.3 bits), Expect = 4.1e-25, P = 4.1e-25
Identities = 56/158 (35%), Positives = 77/158 (48%)

```
Query:   54 YRHVDRATGQVLNCDKCPAGTYVSEHCTNTSLRVCSSCPVGTFTRHENGIEKCHDCSQPC 113
             |  |  |  |||||  ||||+ +|||    ||+ ||   +|   +  ++| ||  |
Sbjct:   28 YLHYDEETSHQLLCDKCPPGTYLKQHCTAKWKTVCAPCPDHYYTDSWHTSDECLYCSPVC 87

Query:  114 PWPMIEKLPCAALTDRECTCPPGMFQSNATCAPHTVCPVGWGVRKKGTETEDVRCKQCAR 173
             |  |    +| |  | +     |  | || |+|| + ||   + +||+|
Sbjct:   88 KELQYVKQECNRTHNRVCECKEGRYLEIEFCLKHRSCPPGFGVVQAGTPERNTVCKRCPD 147

Query:  174 GTFSDVPSSVMKCKAYTDCLSQNLVVIKPGTKETDNVC 211
             | |||+  ||   |+ +|+|    |++ +  |   ||+|
Sbjct:  148 GFFSNETSSKAPCRKHTNCSVFGLLLTQKGNATHDNIC 185
```

Fig. 3

TUMOR NECROSIS FACTOR RECEPTOR - HOMO SAPIENS (HUMAN), 425 aa.

Length = 425

Score = 293 (103.1 bits), Expect = 5.8e-26, P = 5.8e-26
Identities = 72/189 (38%), Positives = 91/189 (48%)

```
Query:   61 TGQVLNCDKCPAGTYVSEHCTNTSLRVCSSCPVGTFTRHENGIEKCHDCSQPCPWPMIEK 120
              | +  |||  +    ||||  ||||     |+|+  + +|        |     +|
Sbjct:   13 TAQMC-CSKCSPGQHAKVFCTKTSDTVCDSCEDSTYTQLWNWVPECLSCGSRCSSDQVET 71

Query:  121 LPCAALTDRECTCPPGMF-----QSNAT-CAPHTVCPVGWGVRKKGTETEDVRCKQCARG 174
             |   +|  ||| || +       |    ||| |   |+| + || ++|| || ||  |
Sbjct:   72 QACTREQNRICTCRPGWYCALSKQEGCRLCAPLRKCRPGFGVARPGTETSDVVCKPCAPG 131

Query:  175 TFSDVPSSVMKCKAYTDCLSQNLVVIKPGTKETDNVCGTLPSFSSSTSPSPGTAIFPRP- 233
             |||+ ||   |+ + +    |+| ||   |||   | + +|    |+
Sbjct:  132 TFSNTTSSTDICRPHQIC---NVVAI-PGNASMDAVC----TSTSPTRSMAPGAVHLPQPV 184

Query:  234 --EHMETHEVPSSTYVP 248
                |   + |
Sbjct:  185 STRSQHTQPTPEPSTAP 201
```

Fig. 4

```
  1
    CCGGTTCAGCCATGGGGACCTCTCCGAGCAGCAGCACCGCCCTCG
              MetGlyThrSerProSerSerSerThrAlaLeuA
 46
    CCTCCTGCAGCCGCATCGCCCGCCGAGCCACAGCCACGATGATCG
    laSerCysSerArgIleAlaArgArgAlaThrAlaThrMetIleA
 91
    CGGGCTCCCTTCTCCTGCTTGGATTCCTTAGCACCACCACAGCTC
    laGlySerLeuLeuLeuLeuGlyPheLeuSerThrThrThrAlaG
136
    AGCCAGAACAGAAGGCCTCGAATCTCATTGGCACATACCGCCATG
    lnProGluGlnLysAlaSerAsnLeuIleGlyThrTyrArgHisV
181
    TTGACCGTGCCACCGGCCAGGTGCTAACCTGTGACAAGTGTCCAG
    alAspArgAlaThrGlyGlnValLeuThrCysAspLysCysProA
226
    CAGGAACCTATGTCTCTGAGCATTGTACCAACACAAGCCTGCGCG
    laGlyThrTyrValSerGluHisCysThrAsnThrSerLeuArgV
271
    TCTGCAGCAGTTGCCCTGTGGGGACCTTTACCAGGCATGAGAATG
    alCysSerSerCysProValGlyThrPheThrArgHisGluAsnG
316
    GCATAGAGAAATGCCATGACTGTAGTCAGCCATGCCCATGGCCAA
    lyIleGluLysCysHisAspCysSerGlnProCysProTrpProM
361
    TGATTGAGAAATTACCTTGTGCTGCCTTGACTGACCGAGAATGCA
    etIleGluLysLeuProCysAlaAlaLeuThrAspArgGluCysT
406
    CTTGCCCACCTGGCATGTTCCAGTCTAACGCTACCTGTGCCCCCC
    hrCysProProGlyMetPheGlnSerAsnAlaThrCysAlaProH
451
    ATACGGTGTGTCCTGTGGGTTGGGGTGTGCGGAAGAAAGGGACAG
    isThrValCysProValGlyTrpGlyValArgLysLysGlyThrG
496
    AGACTGAGGATGTGCGGTGTAAGCAGTGTGCTCGGGGTACCTTCT
    luThrGluAspValArgCysLysGlnCysAlaArgGlyThrPheS
541
    CAGATGTGCCTTCTAGTGTGATGAAATGCAAAGCATACACAGACT
    erAspValProSerSerValMetLysCysLysAlaTyrThrAspC
586
    GTCTGAGTCAGAACCTGGTGGTGATCAAGCCGGGGACCAAGGAGA
    ysLeuSerGlnAsnLeuValValIleLysProGlyThrLysGluT
631
    CAGACAACGTCTGTGGCACACTCCCGTCCTTCTCCAGCTCCACCT
    hrAspAsnValCysGlyThrLeuProSerPheSerSerSerThrS
676
    CACCTTCCCCTGGCACAGCCATCTTTCCACGCCCTGAGCACATGG
    erProSerProGlyThrAlaIlePheProArgProGluHisMetG
721
    AAACCCATGAAGTCCCTTCCTCCACTTATGTTCCCAAAGGTAACT
    luThrHisGluValProSerSerThrTyrValProLysGlyAsnL
766
    TAACCTCA
    euThrSer
```

Fig. 5

```
  1
    GCGNCCGCGNNGNGNGCAAGGTGCTGAGCGCCCCTAGAGCCTCCC
 46
    TTGCCGCCTCCCTCCTCTGCCCGGCCGTAGCAGTGCACATGGGGT
 91
    GTTGGAGGTAGATGGGCTCCCGGCCGGGAGGCGGCGGTGGATGCG
                    MetGlySerArgProGlyGlyGlyGlyCysG
136
    GCGCTGGGCAGAAGCAGCCGCCGATTCCAGCTGCCCCGCGCGCCC
    lyAlaGlyGlnLysGlnProProIleProAlaAlaProArgAlaP
181
    CGGCCCCCTTGCGAGTCCCCGGTTCAGCCATGGGGACCTCTCCGA
    roAlaProLeuArgValProGlySerAlaMetGlyThrSerProS
226
    GCAGCAGCACCTCCCTCGCCTCCTGCAGCCGCATCGCCCGCCGAG
    erSerSerThrSerLeuAlaSerCysSerArgIleAlaArgArgA
271
    CCACAGCCACTATGATCGCGGGCTCCCTTCTCCTGCTTGGATTCC
    laThrAlaThrMetIleAlaGlySerLeuLeuLeuLeuGlyPheL
316
    TTAGCACCACCACAGCTCAGCCAGAACAGAAGGCCTCGAATCTCA
    euSerThrThrThrAlaGlnProGluGlnLysAlaSerAsnLeuI
361
    TTGGCACATACCGCCATGTTGACCGTGCCACCGGCCAGGTGCTTA
    leGlyThrTyrArgHisValAspArgAlaThrGlyGlnValLeuA
406
    ACTGTGACAAGTGTCCAGCAGGAACCTATGTCTCTGAGCATTGTA
    snCysAspLysCysProAlaGlyThrTyrValSerGluHisCysT
451
    CCAACACAAGCCTGCGCGTCTGCAGCAGTTGCCCTGTGGGGACCT
    hrAsnThrSerLeuArgValCysSerSerCysProValGlyThrP
496
    TTACCAGGCATGAGAATGGCATAGAGAAATGCCATGACTGTAGTC
    heThrArgHisGluAsnGlyIleGluLysCysHisAspCysSerG
541
    AGCCATGCCCATGGCCAATGATTGAGAAATTACCTTGTGCTGCCT
    lnProCysProTrpProMetIleGluLysLeuProCysAlaAlaL
586
    TGACTGACCGAGAATGCACTTGCCCACCTGGCATGTTCCAGTCTA
    euThrAspArgGluCysThrCysProProGlyMetPheGlnSerA
631
    ACGCTACCTGTGCCCCCCATACGGTGTGTCCTGTGGGTTGGGGTG
    snAlaThrCysAlaProHisThrValCysProValGlyTrpGlyV
676
    TGCGGAAGAAAGGGACAGAGACTGAGGATGTGCGGTGTAAGCAGT
    alArgLysLysGlyThrGluThrGluAspValArgCysLysGlnC
721
    GTGCTCGGGGTACCTTCTCAGATGTGCCTTCTAGTGTGATGAAAT
    ysAlaArgGlyThrPheSerAspValProSerSerValMetLysC
766
    GCAAAGCATACACAGACTGTCTGAGTCAGAACCTGGTGGTGATCA
    ysLysAlaTyrThrAspCysLeuSerGlnAsnLeuValValIleL
811
    AGCCGGGGACCAAGGAGACAGACAACGTCTGTGGCACACTCCCGT
    ysProGlyThrLysGluThrAspAsnValCysGlyThrLeuProS
856
    CCTTCTCCAGCTCCACCTCACCTTCCCCTGGCACAGCCATCTTTC
    erPheSerSerSerThrSerProSerProGlyThrAlaIlePheP
901
    CACGCCCTGAGCACATGGAAACCCATGAAGTCCCTTCCTCCACTT
    roArgProGluHisMetGluThrHisGluValProSerSerThrT
946
    ATGTTCCCAAAGGTAACTTAACCTCATGAATTATTTATTTGAGGA
    YrValProLysGlyAsnLeuThrSer
```

Fig. 6A

```
991
     AGGCTTTGAGCCCAGTGGAGGTACCAAGAGTGGGCTTATACCAAA
1036
     GATGTTTTCTCCATTTCGTGTATTCCAAAGTCACCCCTTGGAGAG
1081
     AGGCCTTCATATGGTGGCTAATTAAATCTGGCTTTTTTGGACTTA
1126
     ATAGAAACATGTAGACTCAGAATTTTTCTGTTAGGGGAGATCAGA
1171
     TATCTAAAAANTAGGTCACATCAAGCTATAAAATATGAACCAAGA
1216
     GAANCAAGGACAGCGTGTGACCTTATGTAAGTTACTTAACCTCTT
1261
     CAGGCCTCAGTTTCAAACTTGTCAAACAAATGAATAATTTAGATG
1306
     TTTAAGGTTCCTTCCAGATCAAAAGTTTTCCAACATGGAGTCAGT
1351
     CCCAGGTAGACATAGCCAGGAGCAGAGAAGAGGGAGAAAGGAAGA
1396
     AAATACCATTACATCCGGAAGCGAGAGATGAATTTTGAATCCAGG
1441
     TGGGGCAAAGAATGGGTAGGAAAGTTAGAAGCTCAGGAAATAAGC
1486
     AAATTTGTATCAGATTGAAGGTAACTAGCACTCATGTCTGGAAAA
1531
     TAATAACTTTATTTTTTCCAAATGATTTTAACTTTACTCCTTATA
1576
     TCAATTATTCAAGTTTTCCATCAGAACCTCAAGCAGAATATAAAA
1621
     TTTATCCTTTATTTTCAAATCCTTTTTGATTTAATGTAATTTTCA
1666
     TGAGATGATGACCAACTTGAG
```

Fig. 6B

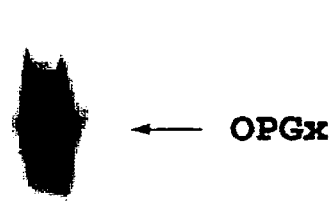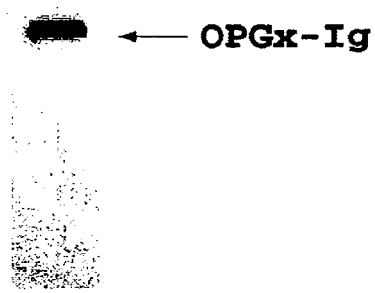
Fig. 7A  Fig. 7B
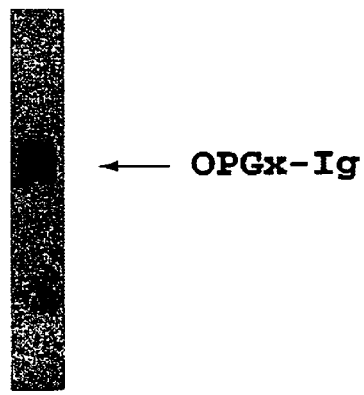
Fig. 8

A. DNA sequence of murine OPGx:

```
   1  GGCCATGGGGACCCGGGCAAGCAGCATCACCGCCCTCGCCTCTTGCAGCCGCACCGCCGGCCAAGTCGGAGCCACGATGG
  81  TCGCCGGCTCTCTTCTCCTGCTTGGATTCCTCAGCACCATCACAGCTCAACCAGAACAAAAGACTCTGAGTCTCCCTGGC
 161  ACCTACCGCCATGTTGACCGTACCACTGGCCAGGTGCTAACCTGCGACAAGTGCCCAGCAGGAACGTATGTCTCCGAGCA
 241  CTGTACCAACATGAGCCTGCGAGTCTGCAGCAGCTGCCCCGCGGGGACCTTTACCAGGCACGAGAACGGCATAGAGAGAT
 321  GCCATGACTGTAGTCAGCCATGTCCATGGCCGATGATTGAGAGATTACCTTGTGCTGCCTTGACTGACCGAGAGTGCATC
 401  TGCCCACCTGGAATGTATCAGTCTAATGGTACCTGCGCTCCCCATACAGTGTGCCCCGTGGGCTGGGGTGTGCGGAAGAA
 481  AGGGACAGAGAATGAAGATGTGCGCTGTAAGCAGTGCGCTCGGGGTACCTTCTCTGACGTGCCTTCCAGTGTGATGAAGT
 561  GTAAAGCTCACACGGACTGTCTGGGTCAGAACCTGGAGGTGGTCAAGCCAGGGACCAAGGAGACAGACAACGTCTGTGGC
 641  ATGCGCCTGTTCTTCTCCAGCACAAACCCACCTTCCTCTGGCACAGTTACCTTTTCTCACCCTGAGCATATGGAATCCCA
 721  CGATGTCCCTTCCTCCACCTATGAGCCCCAAGGCATGAACTCAACAGATTCCAACTCTACTGCCTCTGTTAGAACTAAGG
 801  TACCAAGTGGCATCGAGGAAGGGACAGTGCCTGACAATACGAGCCCAACCAGTGGGAAGGAAGGCACTAATAGGACCCTG
 881  CCAAACCCACCACAAGTTACCCACCAGCAAGCCCCCACCACAGACACATTCTGAAGCTGCTGCCATCGTCCATGAAGGC
 961  CACGGGTGAGAAGTCCAGCACAGCCATCAAGGCCCCCAAGAGGGGTCACCCCAGACAGAACGCTCACAAGCATTTCGACA
1041  TCAACGAGCACTTGCCTTGGATGATCGTCCTCTTCCTTCTGCTGGTCCTGGTGCTGATAGTGGTGTGCAGTATCCGAAAG
1121  AGCTCCAGGACTCTCAAAAAGGGGCCCCGGCAGGATCCCAGCGCCATAGTGGAAAAGGCGGGGCTGAAGAAGTCCCTGAC
1201  TCCCACCCAGAACCGGGAGAAATGGATCTACTACCGCAACGGCCATGGTATTGACATCTTGAAGCTTGTAGCAGCCCAGG
1281  TGGGAAGCCAGTGGAAGGACATCTATCAGTTTCTTTGCAACGCCAGCGAGAGGGAGGTGGCGGCCTTCTCCAATGGATAC
1361  ACTGCAGATCACGAACGGGCCTACGCGGCTCTGCAGCACTGGACCATCCGTGGCCCTGAGGCCAGCCTTGCCCAGCTCAT
1441  TAGCGCCTTGCGCCAGCACCGACGCAATGATGTTGTGGAGAAGATTCGTGGGCTGATGGAAGACACCACACAGTTGGAAA
1521  CAGACAAACTGGCTCTCCCCATGAGCCCCAGTCCGCTGAGCCCGAGCCCCATCCCCAGTCCTAACGTGAAACTTGAGAAT
1601  TCCACTCTCCTGACAGTGGAGCCCTCACCGCTGGACAAGAACAAGTGCTTCTTCGTGGACGAAGTCAGAGCCCCTTCTGC
1681  GTTGCGACTCCACATCCAGTGGCTCTTCAGCACTGAGCAGAAACGGCTCCTTTATTACCAAAGGTACCCATCTCTTGTGA
1761  AGCCTGGGGCCATCTTCCTTGACACTCCACAGCGCAGTTGTAGCTGAGCCCACTTGAATGACCTGTTAGGAGACCTCCAA
1841  GATGAAAGTGTCCTCAAGGAAGCCACATCACTAATTAACATGGATACNCCTAGAAAGTCTTTACAACTTGTGCCCTATCC
1921  AGAACCAGCTTTGATACAGGCCCATTAGCGTCTATCCTTGGCATACTATCCAATGTGTGCTTCAGGAGACATCTGACAAA
2001  AGACAGTGTAGCTGATCTGGAGAATTATTTCCCACACTTGCTGAGTCTAAGGCTGAAGAGTGAAACCCATCTGGAGAGTC
2081  AGAAGTAGTTTTAGTGTTTAGAATTGATCCTAAAATTCACTCTAAACTAGATTGCACACATTTTCAGCATAGTAGGGGAG
2161  GGGGCTAGGGCTCAGTTGGTAAGGTGCCTGCCTAGCAGGCATGAAGCCCAGCAGACACAAAAACAGAGTGTGGTGGCTCT
2241  CAGTTGGTATTTTAGCATTTGAGAAAATATGCAATTCAAAGTCAGCTGGGTGTGGTGGGAGACTCCTTTGATCCCAGCAC
2321  TTAAGAAAGAGAGCTAGAATTCAGCGGCCGCTTTTTTTTACCTGCCCGGGCGGCCGCTCGAGCCCTATAGTGAG
```

Fig. 9A

B. Protein sequence of murine OPGx:

```
  1  MGTRASSITALASCSRTAGQVGATMVAGSLLLLGFLSTITAQPEQKTLSLPGTYRHVDRTTGQVLTCDKCPAGTYVSEHC
 81  TNMSLRVCSSCPAGTFTRHENGIERCHDCSQPCPWPMIERLPCAALTDRECICPPGMYQSNGTCAPHTVCPVGWGVRKKG
161  TENEDVRCKQCARGTFSDVPSSVMKCKAHTDCLGQNLEVVKPGTKETDNVCGMRLFFSSTNPPSSGTVTFSHPEHMESHD
241  VPSSTYEPQGMNSTDSNSTASVRTKVPSGIEEGTVPDNTSPTSGKEGTNRTLPNPPQVTHQQAPHHRHILKLLPSSMKAT
321  GEKSSTAIKAPKRGHPRQNAHKHFDINEHLPWMIVLFLLLVLVLIVVCSIRKSSRTLKKGPRQDPSAIVEKAGLKKSLTP
401  TQNREKWIYYRNGHGIDILKLVAAQVGSQWKDIYQFLCNASEREVAAFSNGYTADHERAYAALQHWTIRGPEASLAQLIS
481  ALRQHRRNDVVEKIRGLMEDTTQLETDKLALPMSPSPLSPSPIPSPNVKLENSTLLTVEPSPLDKNKCFFVDEVRAPSAL
561  RLHIQWLFSTEQKRLLYYQRYPSLVKPGAIFLDTPQRSCS
```

Fig. 9B

SEQUENCE LISTING

```
<160> NUMBER OF SEQ ID NOS: 25

<210> SEQ ID NO 1
<211> LENGTH: 1686
<212> TYPE: DNA
<213> ORGANISM: Homo sapiens
<220> FEATURE:
<221> NAME/KEY: CDS
```

-continued

```
<222> LOCATION: (102)..(971)
<221> NAME/KEY: misc_feature
<222> LOCATION: (4)..(15)
<223> OTHER INFORMATION: wherein any n is an a, t, c or g

<400> SEQUENCE: 1
gcgnccgcgn ngngngcaag gtgctgagcg ccctagagc ctcccttgcc gcctccctcc      60 tctgccggc cgcagcagtg cacatggggt gttggaggta g atg ggc tcc cgg ccg     116
                                            Met Gly Ser Arg Pro
                                              1               5 gga ggc ggc ggt gga tgc ggc gct ggg cag aag cag ccg ccg att cca     164
Gly Gly Gly Gly Gly Cys Gly Ala Gly Gln Lys Gln Pro Pro Ile Pro
             10                  15                  20 gct gcc ccg cgc gcc ccg gcc acc ttg cga gtc ccc ggt tca gcc atg     212
Ala Ala Pro Arg Ala Pro Ala Thr Leu Arg Val Pro Gly Ser Ala Met
         25                  30                  35 ggg acc tct ccg agc agc agc acc gcc ctc gcc tcc tgc agc agc atc     260
Gly Thr Ser Pro Ser Ser Ser Thr Ala Leu Ala Ser Cys Ser Ser Ile
     40                  45                  50 gcc cgc cga gcc aca gcc acg atg atc gcg ggc tcc ctt ctc ctg ctt     308
Ala Arg Arg Ala Thr Ala Thr Met Ile Ala Gly Ser Leu Leu Leu Leu
 55                  60                  65 gga ttc ctt agc acc acc aca gct cag cca gaa cag aag gcc tcg aat     356
Gly Phe Leu Ser Thr Thr Thr Ala Gln Pro Glu Gln Lys Ala Ser Asn
 70                  75                  80                  85 ctc att ggc aca tac cgc cat gtt gac cgt gcc acc ggc cag gtg ctc     404
Leu Ile Gly Thr Tyr Arg His Val Asp Arg Ala Thr Gly Gln Val Leu
                 90                  95                 100 aac tgt gac aag tgt cca gca gga acc tat gtc tct gag cat tgt acc     452
Asn Cys Asp Lys Cys Pro Ala Gly Thr Tyr Val Ser Glu His Cys Thr
            105                 110                 115 aac aca agc ctg cgc gtc tgc agc agt tgc cct gtg ggg acc ttt acc     500
Asn Thr Ser Leu Arg Val Cys Ser Ser Cys Pro Val Gly Thr Phe Thr
        120                 125                 130 agg cat gag aat ggc ata gag aaa tgc cat gac tgt agt cag cca tgc     548
Arg His Glu Asn Gly Ile Glu Lys Cys His Asp Cys Ser Gln Pro Cys
    135                 140                 145 cca tgg cca atg att gag aaa tta cct tgt gct gcc ttg act gac cga     596
Pro Trp Pro Met Ile Glu Lys Leu Pro Cys Ala Ala Leu Thr Asp Arg
150                 155                 160                 165 gaa tgc act tgc cca cct ggc atg ttc cag tct aac gct acc tgt gcc     644
Glu Cys Thr Cys Pro Pro Gly Met Phe Gln Ser Asn Ala Thr Cys Ala
                170                 175                 180 ccc cat acg gtg tgt cct gtg ggt tgg ggt gtg cgg aag aaa ggg aca     692
Pro His Thr Val Cys Pro Val Gly Trp Gly Val Arg Lys Lys Gly Thr
            185                 190                 195 gag act gag gat gtg cgg tgt aag cag tgt gct cgg ggt acc ttc tca     740
Glu Thr Glu Asp Val Arg Cys Lys Gln Cys Ala Arg Gly Thr Phe Ser
        200                 205                 210 gat gtg cct tct agt gtg atg aaa tgc aaa gca tac aca gac tgt ctg     788
Asp Val Pro Ser Ser Val Met Lys Cys Lys Ala Tyr Thr Asp Cys Leu
    215                 220                 225 agt cag aac ctg gtg gtg atc aag ccg ggg acc aag gag aca gac aac     836
Ser Gln Asn Leu Val Val Ile Lys Pro Gly Thr Lys Glu Thr Asp Asn
230                 235                 240                 245 gtc tgt ggc aca ctc ccg tcc ttc tcc agc tcc acc tca cct tcc cct     884
Val Cys Gly Thr Leu Pro Ser Phe Ser Ser Ser Thr Ser Pro Ser Pro
                250                 255                 260 ggc aca gcc atc ttt cca cgc cct gag cac atg gaa acc cat gaa gtc     932
Gly Thr Ala Ile Phe Pro Arg Pro Glu His Met Glu Thr His Glu Val
```

```
                   265                 270                 275
cct tcc tcc act tat gtt ccc aaa ggt aac tta acc tca tgaattattt      981
Pro Ser Ser Thr Tyr Val Pro Lys Gly Asn Leu Thr Ser
                   280                 285                 290 atttgaggaa ggctttgagc ccagtggagg taccaagagt gggcttatac caaagatgtt   1041
ttctccattt cgtgtattcc aaagtcaccc cttggagaga ggccttcata tggtggctaa   1101
ttaaatctgg cttttttgga cttaatagaa acatgtagac tcagaatttt tctgttaggg   1161
gagatcagat atctaaaaac taggtcacat caagctataa aatatgaacc aagagaaaca   1221
aggacagcgt gtgaccttat gtaagttact taacctcttc aggcctcagt ttcaaacttg   1281
tcaaacaaat gaataattta gatgtttaag gttccttcca gatcaaaagt tttccaacat   1341
ggagtcagtc ccaggtagac atagccagga gcagagaaga gggagaaagg aagaaaatac   1401 cattcatcc ggaagcgaga gatgaatttt gaatccaggt ggggcaaaga atgggtagga    1461
aagttagaag ctcaggaaat aagcaaattt gtatcagatt gaaggtaact agcactcatg   1521
tctggaaaat aataacttta ttttttccaa atgatttta ctttactcct tatatcaatt    1581
attcaagttt tccatcagaa cctcaagcag aatataaaat ttatcctttta ttttcaaatc  1641 ctttttgatt taatgtaatt ttcatgagat gatgaccaac ttgag                   1686
```

<210> SEQ ID NO 2
<211> LENGTH: 290
<212> TYPE: PRT
<213> ORGANISM: Homo sapiens

<400> SEQUENCE: 2

```
Met Gly Ser Arg Pro Gly Gly Gly Gly Cys Gly Ala Gly Gln Lys
 1               5                  10                  15

Gln Pro Pro Ile Pro Ala Ala Pro Arg Ala Pro Ala Thr Leu Arg Val
                20                  25                  30

Pro Gly Ser Ala Met Gly Thr Ser Pro Ser Ser Ser Thr Ala Leu Ala
            35                  40                  45

Ser Cys Ser Ser Ile Ala Arg Arg Ala Thr Ala Thr Met Ile Ala Gly
        50                  55                  60

Ser Leu Leu Leu Leu Gly Phe Leu Ser Thr Thr Thr Ala Gln Pro Glu
 65                 70                  75                  80

Gln Lys Ala Ser Asn Leu Ile Gly Thr Tyr Arg His Val Asp Arg Ala
                85                  90                  95

Thr Gly Gln Val Leu Asn Cys Asp Lys Cys Pro Ala Gly Thr Tyr Val
            100                 105                 110

Ser Glu His Cys Thr Asn Thr Ser Leu Arg Val Cys Ser Ser Cys Pro
        115                 120                 125

Val Gly Thr Phe Thr Arg His Glu Asn Gly Ile Glu Lys Cys His Asp
    130                 135                 140

Cys Ser Gln Pro Cys Pro Trp Pro Met Ile Glu Lys Leu Pro Cys Ala
145                 150                 155                 160

Ala Leu Thr Asp Arg Glu Cys Thr Cys Pro Pro Gly Met Phe Gln Ser
                165                 170                 175

Asn Ala Thr Cys Ala Pro His Thr Val Cys Pro Val Gly Trp Gly Val
            180                 185                 190

Arg Lys Lys Gly Thr Glu Thr Glu Asp Val Arg Cys Lys Gln Cys Ala
        195                 200                 205

Arg Gly Thr Phe Ser Asp Val Pro Ser Ser Val Met Lys Cys Lys Ala
    210                 215                 220
```

```
Tyr Thr Asp Cys Leu Ser Gln Asn Leu Val Val Ile Lys Pro Gly Thr
225                 230                 235                 240

Lys Glu Thr Asp Asn Val Cys Gly Thr Leu Pro Ser Phe Ser Ser Ser
            245                 250                 255

Thr Ser Pro Ser Pro Gly Thr Ala Ile Phe Pro Arg Pro Glu His Met
        260                 265                 270

Glu Thr His Glu Val Pro Ser Ser Thr Tyr Val Pro Lys Gly Asn Leu
        275                 280                 285

Thr Ser
    290

<210> SEQ ID NO 3
<211> LENGTH: 2271
<212> TYPE: DNA
<213> ORGANISM: Homo sapiens
<220> FEATURE:
<221> NAME/KEY: CDS
<222> LOCATION: (102)..(2174)
<221> NAME/KEY: misc_feature
<222> LOCATION: (4)..(38)
<223> OTHER INFORMATION: wherein any n is an a, t, c, or g

<400> SEQUENCE: 3
gcgnccgcgn ngngngcaag gtgctgagcg cccctagngc ctcccttgcc gcctccctcc      60
tctgcccggc cgtagcagtg cacatggggt gttggaggta g atg ggc tcc cgg ccg    116
                                             Met Gly Ser Arg Pro
                                               1               5 gga ggc ggc ggt gga tgc ggc gct ggg cag aag cag ccg ccg att cca      164
Gly Gly Gly Gly Gly Cys Gly Ala Gly Gln Lys Gln Pro Pro Ile Pro
             10                  15                  20 gct gcc ccg cgc gcc ccg ggc acc ttg cga gtc ccc ggt tca gcc atg      212
Ala Ala Pro Arg Ala Pro Gly Thr Leu Arg Val Pro Gly Ser Ala Met
         25                  30                  35 ggg acc tct ccg agc agc agc acc gcc ctc gcc tcc tgc agc cgc atc      260
Gly Thr Ser Pro Ser Ser Ser Thr Ala Leu Ala Ser Cys Ser Arg Ile
     40                  45                  50 gcc cgc cga gcc aca gcc acg atg atc gcg ggc tcc ctt ctc ctg ctt      308
Ala Arg Arg Ala Thr Ala Thr Met Ile Ala Gly Ser Leu Leu Leu Leu
 55                  60                  65 gga ttc ctt agc acc acc aca gct cag cca gaa cag aag gcc tcg aat      356
Gly Phe Leu Ser Thr Thr Thr Ala Gln Pro Glu Gln Lys Ala Ser Asn
 70                  75                  80                  85 ctc att ggc aca tac cgc cat gtt gac cgt gcc acc ggc cag gtg cta      404
Leu Ile Gly Thr Tyr Arg His Val Asp Arg Ala Thr Gly Gln Val Leu
                 90                  95                 100 acc tgt gac aag tgt cca gca gga acc tat gtc tct gag cat tgt acc      452
Thr Cys Asp Lys Cys Pro Ala Gly Thr Tyr Val Ser Glu His Cys Thr
            105                 110                 115 aac aca agc ctg cgc gtc tgc agc agt tgc cct gtg ggg acc ttt acc      500
Asn Thr Ser Leu Arg Val Cys Ser Ser Cys Pro Val Gly Thr Phe Thr
        120                 125                 130 agg cat gag aat ggc ata gag aaa tgc cat gac tgt agt cag cca tgc      548
Arg His Glu Asn Gly Ile Glu Lys Cys His Asp Cys Ser Gln Pro Cys
    135                 140                 145 cca tgg cca atg att gag aaa tta cct tgt gct gcc ttg act gac cga      596
Pro Trp Pro Met Ile Glu Lys Leu Pro Cys Ala Ala Leu Thr Asp Arg
150                 155                 160                 165 gaa tgc act tgc cca cct ggc atg ttc cag tct aac gct acc tgt gcc      644
Glu Cys Thr Cys Pro Pro Gly Met Phe Gln Ser Asn Ala Thr Cys Ala
                170                 175                 180
```

-continued

| | |
|---|---|
| ccc cat acg gtg tgt cct gtg ggt tgg ggt gtg cgg aag aaa ggg aca<br>Pro His Thr Val Cys Pro Val Gly Trp Gly Val Arg Lys Lys Gly Thr<br>            185                    190                    195 | 692 |
| gag act gag gat gtg cgg tgt aag cag tgt gct cgg ggt acc ttc tca<br>Glu Thr Glu Asp Val Arg Cys Lys Gln Cys Ala Arg Gly Thr Phe Ser<br>            200                    205                    210 | 740 |
| gat gtg cct tct agt gtg atg aaa tgc aaa gca tac aca gac tgt ctg<br>Asp Val Pro Ser Ser Val Met Lys Cys Lys Ala Tyr Thr Asp Cys Leu<br>215                    220                    225 | 788 |
| agt cag aac ctg gtg gtg atc aag ccg ggg acc aag gag aca gac aac<br>Ser Gln Asn Leu Val Val Ile Lys Pro Gly Thr Lys Glu Thr Asp Asn<br>230                    235                    240                    245 | 836 |
| gtc tgt ggc aca ctc ccg tcc ttc tcc agc tcc acc tca cct tcc cct<br>Val Cys Gly Thr Leu Pro Ser Phe Ser Ser Ser Thr Ser Pro Ser Pro<br>            250                    255                    260 | 884 |
| ggc aca gcc atc ttt cca cgc cct gag cac atg gaa acc cat gaa gtc<br>Gly Thr Ala Ile Phe Pro Arg Pro Glu His Met Glu Thr His Glu Val<br>            265                    270                    275 | 932 |
| cct tcc tcc act tat gtt ccc aaa ggc atg aac tca aca gaa tcc aac<br>Pro Ser Ser Thr Tyr Val Pro Lys Gly Met Asn Ser Thr Glu Ser Asn<br>                  280                    285                    290 | 980 |
| tct tct gcc tct gtt aga cca aag gta ctg agt agc atc cag gaa ggg<br>Ser Ser Ala Ser Val Arg Pro Lys Val Leu Ser Ser Ile Gln Glu Gly<br>295                    300                    305 | 1028 |
| aca gtc cct gac aac aca agc tca gca agg ggg aag gaa gac gtg aac<br>Thr Val Pro Asp Asn Thr Ser Ser Ala Arg Gly Lys Glu Asp Val Asn<br>310                    315                    320                    325 | 1076 |
| aag acc ctc cca aac ctt cag gta gtc aac cac cag caa ggc ccc cac<br>Lys Thr Leu Pro Asn Leu Gln Val Val Asn His Gln Gln Gly Pro His<br>                  330                    335                    340 | 1124 |
| cac aga cac atc ctg aag ctg ctg ccg tcc atg gag gcc act ggg ggc<br>His Arg His Ile Leu Lys Leu Leu Pro Ser Met Glu Ala Thr Gly Gly<br>                  345                    350                    355 | 1172 |
| gag aag tcc agc acg ccc atc aag ggc ccc aag agg gga cat cct aga<br>Glu Lys Ser Ser Thr Pro Ile Lys Gly Pro Lys Arg Gly His Pro Arg<br>            360                    365                    370 | 1220 |
| cag aac cta cac aag cat ttt gac atc aat gag cat ttg ccc tgg atg<br>Gln Asn Leu His Lys His Phe Asp Ile Asn Glu His Leu Pro Trp Met<br>375                    380                    385 | 1268 |
| att gtg ctt ttc ctg ctg ctg gtg ctt gtg gtg att gtg gtg tgc agt<br>Ile Val Leu Phe Leu Leu Leu Val Leu Val Val Ile Val Val Cys Ser<br>390                    395                    400                    405 | 1316 |
| atc cgg aaa agc tcg agg act ctg aaa aag ggg ccc cgg cag gat ccc<br>Ile Arg Lys Ser Ser Arg Thr Leu Lys Lys Gly Pro Arg Gln Asp Pro<br>                  410                    415                    420 | 1364 |
| agt gcc att gtg gaa aag gca ggg ctg aag aaa tcc atg act cca acc<br>Ser Ala Ile Val Glu Lys Ala Gly Leu Lys Lys Ser Met Thr Pro Thr<br>425                    430                    435 | 1412 |
| cag aac cgg gag aaa tgg atc tac tac tgc aat ggc cat ggt atc gat<br>Gln Asn Arg Glu Lys Trp Ile Tyr Tyr Cys Asn Gly His Gly Ile Asp<br>            440                    445                    450 | 1460 |
| atc ctg aag ctt gta gca gcc caa gtg gga agc cag tgg aaa gat atc<br>Ile Leu Lys Leu Val Ala Ala Gln Val Gly Ser Gln Trp Lys Asp Ile<br>455                    460                    465 | 1508 |
| tat cag ttt ctt tgc aat gcc agt gag agg gag gtt gct gct ttc tcc<br>Tyr Gln Phe Leu Cys Asn Ala Ser Glu Arg Glu Val Ala Ala Phe Ser<br>470                    475                    480                    485 | 1556 |
| aat ggg tac aca gcc gac cac gag cgg gcc tac gca gct ctg cag cac<br>Asn Gly Tyr Thr Ala Asp His Glu Arg Ala Tyr Ala Ala Leu Gln His | 1604 |

```
                    490               495                500
tgg acc atc cgg ggc ccc gag gcc agc ctc gcc cag cta att agc gcc    1652
Trp Thr Ile Arg Gly Pro Glu Ala Ser Leu Ala Gln Leu Ile Ser Ala
            505               510               515 ctg cgc cag cac cgg aga aac gat gtt gtg gag aag att cgt ggg ctg    1700
Leu Arg Gln His Arg Arg Asn Asp Val Val Glu Lys Ile Arg Gly Leu
            520               525               530 atg gaa gac acc acc cag ctg gaa act gac aaa cta gct ctc ccg atg    1748
Met Glu Asp Thr Thr Gln Leu Glu Thr Asp Lys Leu Ala Leu Pro Met
535               540               545 agc ccc agc ccg ctt agc ccg agc ccc atc ccc agc ccc aac gcg aaa    1796
Ser Pro Ser Pro Leu Ser Pro Ser Pro Ile Pro Ser Pro Asn Ala Lys
550               555               560               565 ctt gag aat tcc gct ctc ctg acg gtg gag cct tcc cca cag gac aag    1844
Leu Glu Asn Ser Ala Leu Leu Thr Val Glu Pro Ser Pro Gln Asp Lys
                570               575               580 aac aag ggc ttc ttc gtg gat gag tcg gag ccc ctt ctc cgc tgt gac    1892
Asn Lys Gly Phe Phe Val Asp Glu Ser Glu Pro Leu Leu Arg Cys Asp
            585               590               595 tct aca tcc agc ggc tcc tcc gcg ctg agc agg aac ggt tcc ttt att    1940
Ser Thr Ser Ser Gly Ser Ser Ala Leu Ser Arg Asn Gly Ser Phe Ile
            600               605               610 acc aaa gaa aag aag gac aca gtg ttg cgg cag gta cgc ctg gac ccc    1988
Thr Lys Glu Lys Lys Asp Thr Val Leu Arg Gln Val Arg Leu Asp Pro
    615               620               625 tgt gac ttg cag cct atc ttt gat gac atg ctc cac ttt cta aat cct    2036
Cys Asp Leu Gln Pro Ile Phe Asp Asp Met Leu His Phe Leu Asn Pro
630               635               640               645 gag gag ctg cgg gtg att gaa gag att ccc cag gct gag gac aaa cta    2084
Glu Glu Leu Arg Val Ile Glu Glu Ile Pro Gln Ala Glu Asp Lys Leu
                650               655               660 gac cgg cta ttc gaa att att gga gtc aag agc cag gaa gcc agc cag    2132
Asp Arg Leu Phe Glu Ile Ile Gly Val Lys Ser Gln Glu Ala Ser Gln
            665               670               675 acc ctc ctg gac tct gtt tat agc cat ctt cct gac ctg ctg             2174
Thr Leu Leu Asp Ser Val Tyr Ser His Leu Pro Asp Leu Leu
            680               685               690 tagaacatta gggatactgc attctggaaa ttactcaatt tagtggcagg gtggttttt    2234 antttctcc tgtttctgat ttttgttgtt tggggtg                             2271

<210> SEQ ID NO 4
<211> LENGTH: 691
<212> TYPE: PRT
<213> ORGANISM: Homo sapiens

<400> SEQUENCE: 4

Met Gly Ser Arg Pro Gly Gly Gly Gly Cys Gly Ala Gly Gln Lys
 1               5                  10                  15

Gln Pro Pro Ile Pro Ala Ala Pro Arg Ala Pro Gly Thr Leu Arg Val
                20                  25                  30

Pro Gly Ser Ala Met Gly Thr Ser Pro Ser Ser Ser Thr Ala Leu Ala
            35                  40                  45

Ser Cys Ser Arg Ile Ala Arg Arg Ala Thr Ala Thr Met Ile Ala Gly
    50                  55                  60

Ser Leu Leu Leu Leu Gly Phe Leu Ser Thr Thr Thr Ala Gln Pro Glu
65                  70                  75                  80

Gln Lys Ala Ser Asn Leu Ile Gly Thr Tyr Arg His Val Asp Arg Ala
                85                  90                  95
```

-continued

Thr Gly Gln Val Leu Thr Cys Asp Lys Cys Pro Ala Gly Thr Tyr Val
            100                 105                 110

Ser Glu His Cys Thr Asn Thr Ser Leu Arg Val Cys Ser Cys Pro
            115                 120                 125

Val Gly Thr Phe Thr Arg His Glu Asn Gly Ile Glu Lys Cys His Asp
            130                 135                 140

Cys Ser Gln Pro Cys Pro Trp Pro Met Ile Glu Lys Leu Pro Cys Ala
145                 150                 155                 160

Ala Leu Thr Asp Arg Glu Cys Thr Cys Pro Pro Gly Met Phe Gln Ser
                165                 170                 175

Asn Ala Thr Cys Ala Pro His Thr Val Cys Pro Val Gly Trp Gly Val
            180                 185                 190

Arg Lys Lys Gly Thr Glu Thr Glu Asp Val Arg Cys Lys Gln Cys Ala
            195                 200                 205

Arg Gly Thr Phe Ser Asp Val Pro Ser Ser Val Met Lys Cys Lys Ala
            210                 215                 220

Tyr Thr Asp Cys Leu Ser Gln Asn Leu Val Val Ile Lys Pro Gly Thr
225                 230                 235                 240

Lys Glu Thr Asp Asn Val Cys Gly Thr Leu Pro Ser Phe Ser Ser Ser
                245                 250                 255

Thr Ser Pro Ser Pro Gly Thr Ala Ile Phe Pro Arg Pro Glu His Met
            260                 265                 270

Glu Thr His Glu Val Pro Ser Ser Thr Tyr Val Pro Lys Gly Met Asn
            275                 280                 285

Ser Thr Glu Ser Asn Ser Ser Ala Ser Val Arg Pro Lys Val Leu Ser
            290                 295                 300

Ser Ile Gln Glu Gly Thr Val Pro Asp Asn Thr Ser Ser Ala Arg Gly
305                 310                 315                 320

Lys Glu Asp Val Asn Lys Thr Leu Pro Asn Leu Gln Val Val Asn His
                325                 330                 335

Gln Gln Gly Pro His His Arg His Ile Leu Lys Leu Leu Pro Ser Met
            340                 345                 350

Glu Ala Thr Gly Gly Glu Lys Ser Ser Thr Pro Ile Lys Gly Pro Lys
            355                 360                 365

Arg Gly His Pro Arg Gln Asn Leu His Lys His Phe Asp Ile Asn Glu
            370                 375                 380

His Leu Pro Trp Met Ile Val Leu Phe Leu Leu Leu Val Leu Val Val
385                 390                 395                 400

Ile Val Val Cys Ser Ile Arg Lys Ser Ser Arg Thr Leu Lys Lys Gly
                405                 410                 415

Pro Arg Gln Asp Pro Ser Ala Ile Val Glu Lys Ala Gly Leu Lys Lys
            420                 425                 430

Ser Met Thr Pro Thr Gln Asn Arg Glu Lys Trp Ile Tyr Tyr Cys Asn
            435                 440                 445

Gly His Gly Ile Asp Ile Leu Lys Leu Val Ala Ala Gln Val Gly Ser
            450                 455                 460

Gln Trp Lys Asp Ile Tyr Gln Phe Leu Cys Asn Ala Ser Glu Arg Glu
465                 470                 475                 480

Val Ala Ala Phe Ser Asn Gly Tyr Thr Ala Asp His Glu Arg Ala Tyr
                485                 490                 495

Ala Ala Leu Gln His Trp Thr Ile Arg Gly Pro Glu Ala Ser Leu Ala
            500                 505                 510

```
Gln Leu Ile Ser Ala Leu Arg Gln His Arg Arg Asn Asp Val Val Glu
            515                 520                 525

Lys Ile Arg Gly Leu Met Glu Asp Thr Thr Gln Leu Glu Thr Asp Lys
        530                 535                 540

Leu Ala Leu Pro Met Ser Pro Ser Pro Leu Ser Pro Ser Pro Ile Pro
545                 550                 555                 560

Ser Pro Asn Ala Lys Leu Glu Asn Ser Ala Leu Leu Thr Val Glu Pro
                565                 570                 575

Ser Pro Gln Asp Lys Asn Lys Gly Phe Phe Val Asp Glu Ser Glu Pro
            580                 585                 590

Leu Leu Arg Cys Asp Ser Thr Ser Gly Ser Ser Ala Leu Ser Arg
        595                 600                 605

Asn Gly Ser Phe Ile Thr Lys Glu Lys Asp Thr Val Leu Arg Gln
    610                 615                 620

Val Arg Leu Asp Pro Cys Asp Leu Gln Pro Ile Phe Asp Asp Met Leu
625                 630                 635                 640

His Phe Leu Asn Pro Glu Glu Leu Arg Val Ile Glu Glu Ile Pro Gln
                645                 650                 655

Ala Glu Asp Lys Leu Asp Arg Leu Phe Glu Ile Ile Gly Val Lys Ser
            660                 665                 670

Gln Glu Ala Ser Gln Thr Leu Leu Asp Ser Val Tyr Ser His Leu Pro
        675                 680                 685

Asp Leu Leu
    690

<210> SEQ ID NO 5
<211> LENGTH: 773
<212> TYPE: DNA
<213> ORGANISM: Homo sapiens
<220> FEATURE:
<221> NAME/KEY: CDS
<222> LOCATION: (12)..(773)

<400> SEQUENCE: 5
ccggttcagc c atg ggg acc tct ccg agc agc agc acc gcc ctc gcc tcc      50
             Met Gly Thr Ser Pro Ser Ser Ser Thr Ala Leu Ala Ser
               1               5                  10 tgc agc cgc atc gcc cgc cga gcc aca gcc acg atg atc gcg ggc tcc      98
Cys Ser Arg Ile Ala Arg Arg Ala Thr Ala Thr Met Ile Ala Gly Ser
 15                  20                  25 ctt ctc ctg ctt gga ttc ctt agc acc acc aca gct cag cca gaa cag     146
Leu Leu Leu Leu Gly Phe Leu Ser Thr Thr Thr Ala Gln Pro Glu Gln
 30                  35                  40                  45 aag gcc tcg aat ctc att ggc aca tac cgc cat gtt gac cgt gcc acc     194
Lys Ala Ser Asn Leu Ile Gly Thr Tyr Arg His Val Asp Arg Ala Thr
                 50                  55                  60 ggc cag gtg cta acc tgt gac aag tgt cca gca gga acc tat gtc tct     242
Gly Gln Val Leu Thr Cys Asp Lys Cys Pro Ala Gly Thr Tyr Val Ser
             65                  70                  75 gag cat tgt acc aac aca agc ctg cgc gtc tgc agc agt tgc cct gtg     290
Glu His Cys Thr Asn Thr Ser Leu Arg Val Cys Ser Ser Cys Pro Val
         80                  85                  90 ggg acc ttt acc agg cat gag aat ggc ata gag aaa tgc cat gac tgt     338
Gly Thr Phe Thr Arg His Glu Asn Gly Ile Glu Lys Cys His Asp Cys
     95                 100                 105 agt cag cca tgc cca tgg cca atg att gag aaa tta cct tgt gct gcc     386
Ser Gln Pro Cys Pro Trp Pro Met Ile Glu Lys Leu Pro Cys Ala Ala
110                 115                 120                 125
```

-continued

```
ttg act gac cga gaa tgc act tgc cca cct ggc atg ttc cag tct aac       434
Leu Thr Asp Arg Glu Cys Thr Cys Pro Pro Gly Met Phe Gln Ser Asn
        130                 135                 140 gct acc tgt gcc ccc cat acg gtg tgt cct gtg ggt tgg ggt gtg cgg       482
Ala Thr Cys Ala Pro His Thr Val Cys Pro Val Gly Trp Gly Val Arg
145                 150                 155 aag aaa ggg aca gag act gag gat gtg cgg tgt aag cag tgt gct cgg       530
Lys Lys Gly Thr Glu Thr Glu Asp Val Arg Cys Lys Gln Cys Ala Arg
        160                 165                 170 ggt acc ttc tca gat gtg cct tct agt gtg atg aaa tgc aaa gca tac       578
Gly Thr Phe Ser Asp Val Pro Ser Ser Val Met Lys Cys Lys Ala Tyr
175                 180                 185 aca gac tgt ctg agt cag aac ctg gtg gtg atc aag ccg ggg acc aag       626
Thr Asp Cys Leu Ser Gln Asn Leu Val Val Ile Lys Pro Gly Thr Lys
190                 195                 200                 205 gag aca gac aac gtc tgt ggc aca ctc ccg tcc ttc tcc agc tcc acc       674
Glu Thr Asp Asn Val Cys Gly Thr Leu Pro Ser Phe Ser Ser Ser Thr
                210                 215                 220 tca cct tcc cct ggc aca gcc atc ttt cca cgc cct gag cac atg gaa       722
Ser Pro Ser Pro Gly Thr Ala Ile Phe Pro Arg Pro Glu His Met Glu
            225                 230                 235 acc cat gaa gtc cct tcc tcc act tat gtt ccc aaa ggt aac tta acc       770
Thr His Glu Val Pro Ser Ser Thr Tyr Val Pro Lys Gly Asn Leu Thr
        240                 245                 250 tca                                                                   773
Ser
```

<210> SEQ ID NO 6
<211> LENGTH: 254
<212> TYPE: PRT
<213> ORGANISM: Homo sapiens

<400> SEQUENCE: 6

```
Met Gly Thr Ser Pro Ser Ser Thr Ala Leu Ala Ser Cys Ser Arg
  1               5                  10                  15

Ile Ala Arg Arg Ala Thr Ala Thr Met Ile Ala Gly Ser Leu Leu Leu
                20                  25                  30

Leu Gly Phe Leu Ser Thr Thr Thr Ala Gln Pro Glu Gln Lys Ala Ser
            35                  40                  45

Asn Leu Ile Gly Thr Tyr Arg His Val Asp Arg Ala Thr Gly Gln Val
        50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190
```

```
Leu Ser Gln Asn Leu Val Val Ile Lys Pro Gly Thr Lys Glu Thr Asp
        195                 200                 205

Asn Val Cys Gly Thr Leu Pro Ser Phe Ser Ser Thr Ser Pro Ser
210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Asn Leu Thr Ser
                245                 250

<210> SEQ ID NO 7
<211> LENGTH: 1686
<212> TYPE: DNA
<213> ORGANISM: Homo sapiens
<220> FEATURE:
<221> NAME/KEY: CDS
<222> LOCATION: (102)..(971)
<221> NAME/KEY: misc_feature
<222> LOCATION: (1)
<223> OTHER INFORMATION: wherein any n is an a, t, c, or g

<400> SEQUENCE: 7
```

| | |
|---|---|
| gcgnccgcgn ngngngcaag gtgctgagcg ccctagagc ctcccttgcc gcctccctcc | 60 |
| tctgcccggc cgtagcagtg cacatggggt gttggaggta g atg ggc tcc cgg ccg<br>                                                                  Met Gly Ser Arg Pro<br>                                                                   1              5 | 116 |
| gga ggc ggc ggt gga tgc ggc gct ggg cag aag cag ccg ccg att cca<br>Gly Gly Gly Gly Gly Cys Gly Ala Gly Gln Lys Gln Pro Pro Ile Pro<br>                  10                  15                  20 | 164 |
| gct gcc ccg cgc gcc ccg gcc ccc ttg cga gtc ccc ggt tca gcc atg<br>Ala Ala Pro Arg Ala Pro Ala Pro Leu Arg Val Pro Gly Ser Ala Met<br>        25                  30                  35 | 212 |
| ggg acc tct ccg agc agc agc acc tcc ctc gcc tcc tgc agc cgc atc<br>Gly Thr Ser Pro Ser Ser Ser Thr Ser Leu Ala Ser Cys Ser Arg Ile<br>      40                  45                  50 | 260 |
| gcc cgc cga gcc aca gcc act atg atc gcg ggc tcc ctt ctc ctg ctt<br>Ala Arg Arg Ala Thr Ala Thr Met Ile Ala Gly Ser Leu Leu Leu Leu<br>55                  60                  65 | 308 |
| gga ttc ctt agc acc acc aca gct cag cca gaa cag aag gcc tcg aat<br>Gly Phe Leu Ser Thr Thr Thr Ala Gln Pro Glu Gln Lys Ala Ser Asn<br>70                  75                  80                  85 | 356 |
| ctc att ggc aca tac cgc cat gtt gac cgt gcc acc ggc cag gtg ctt<br>Leu Ile Gly Thr Tyr Arg His Val Asp Arg Ala Thr Gly Gln Val Leu<br>                90                  95                  100 | 404 |
| aac tgt gac aag tgt cca gca gga acc tat gtc tct gag cat tgt acc<br>Asn Cys Asp Lys Cys Pro Ala Gly Thr Tyr Val Ser Glu His Cys Thr<br>            105                  110                  115 | 452 |
| aac aca agc ctg cgc gtc tgc agc agt tgc cct gtg ggg acc ttt acc<br>Asn Thr Ser Leu Arg Val Cys Ser Ser Cys Pro Val Gly Thr Phe Thr<br>120                  125                  130 | 500 |
| agg cat gag aat ggc ata gag aaa tgc cat gac tgt agt cag cca tgc<br>Arg His Glu Asn Gly Ile Glu Lys Cys His Asp Cys Ser Gln Pro Cys<br>            135                  140                  145 | 548 |
| cca tgg cca atg att gag aaa tta cct tgt gct gcc ttg act gac cga<br>Pro Trp Pro Met Ile Glu Lys Leu Pro Cys Ala Ala Leu Thr Asp Arg<br>150                  155                  160                  165 | 596 |
| gaa tgc act tgc cca cct ggc atg ttc cag tct aac gct acc tgt gcc<br>Glu Cys Thr Cys Pro Pro Gly Met Phe Gln Ser Asn Ala Thr Cys Ala<br>                170                  175                  180 | 644 |
| ccc cat acg gtg tgt cct gtg ggt tgg ggt gtg cgg aag aaa ggg aca<br>Pro His Thr Val Cys Pro Val Gly Trp Gly Val Arg Lys Lys Gly Thr<br>                185                  190                  195 | 692 |

```
gag act gag gat gtg cgg tgt aag cag tgt gct cgg ggt acc ttc tca       740
Glu Thr Glu Asp Val Arg Cys Lys Gln Cys Ala Arg Gly Thr Phe Ser
            200                 205                 210 gat gtg cct tct agt gtg atg aaa tgc aaa gca tac aca gac tgt ctg       788
Asp Val Pro Ser Ser Val Met Lys Cys Lys Ala Tyr Thr Asp Cys Leu
        215                 220                 225 agt cag aac ctg gtg gtg atc aag ccg ggg acc aag gag aca gac aac       836
Ser Gln Asn Leu Val Val Ile Lys Pro Gly Thr Lys Glu Thr Asp Asn
230                 235                 240                 245 gtc tgt ggc aca ctc ccg tcc ttc tcc agc tcc acc tca cct tcc cct       884
Val Cys Gly Thr Leu Pro Ser Phe Ser Ser Ser Thr Ser Pro Ser Pro
                250                 255                 260 ggc aca gcc atc ttt cca cgc cct gag cac atg gaa acc cat gaa gtc       932
Gly Thr Ala Ile Phe Pro Arg Pro Glu His Met Glu Thr His Glu Val
            265                 270                 275 cct tcc tcc act tat gtt ccc aaa ggt aac tta acc tca tgaattattt       981
Pro Ser Ser Thr Tyr Val Pro Lys Gly Asn Leu Thr Ser
        280                 285                 290 atttgaggaa ggctttgagc ccagtggagg taccaagagt gggcttatac caaagatgtt      1041
ttctccattt cgtgtattcc aaagtcaccc cttggagaga ggccttcata tggtggctaa      1101
ttaaatctgg cttttttgga cttaatagaa acatgtagac tcagaatttt tctgttaggg      1161
gagatcagat atctaaaaan taggtcacat caagctataa aatatgaacc aagagaanca      1221
aggacagcgt gtgaccttat gtaagttact taacctcttc aggcctcagt ttcaaacttg      1281
tcaaacaaat gaataattta gatgtttaag gttccttcca gatcaaaagt tttccaacat      1341
ggagtcagtc ccaggtagac atagccagga gcagagaaga gggagaaagg aagaaaatac      1401
cattacatcc ggaagcgaga gatgaatttt gaatccaggt ggggcaaaga atgggtagga      1461
aagttagaag ctcaggaaat aagcaaattt gtatcagatt gaaggtaact agcactcatg      1521
tctggaaaat aataacttta ttttttccaa atgattttaa ctttactcct tatatcaatt      1581
attcaagttt tccatcagaa cctcaagcag aatataaaat ttatcccttta ttttcaaatc      1641 cttttttgatt taatgtaatt ttcatgagat gatgaccaac ttgag                     1686

<210> SEQ ID NO 8
<211> LENGTH: 290
<212> TYPE: PRT
<213> ORGANISM: Homo sapiens

<400> SEQUENCE: 8

Met Gly Ser Arg Pro Gly Gly Gly Gly Cys Gly Ala Gly Gln Lys
1               5                   10                  15

Gln Pro Pro Ile Pro Ala Ala Pro Arg Ala Pro Ala Pro Leu Arg Val
            20                  25                  30

Pro Gly Ser Ala Met Gly Thr Ser Pro Ser Ser Thr Ser Leu Ala
        35                  40                  45

Ser Cys Ser Arg Ile Ala Arg Arg Ala Thr Ala Thr Met Ile Ala Gly
    50                  55                  60

Ser Leu Leu Leu Leu Gly Phe Leu Ser Thr Thr Thr Ala Gln Pro Glu
65                  70                  75                  80

Gln Lys Ala Ser Asn Leu Ile Gly Thr Tyr Arg His Val Asp Arg Ala
                85                  90                  95

Thr Gly Gln Val Leu Asn Cys Asp Lys Cys Pro Ala Gly Thr Tyr Val
            100                 105                 110

Ser Glu His Cys Thr Asn Thr Ser Leu Arg Val Cys Ser Ser Cys Pro
```

```
                115               120                  125
Val Gly Thr Phe Thr Arg His Glu Asn Gly Ile Glu Lys Cys His Asp
    130                 135                 140

Cys Ser Gln Pro Cys Pro Trp Pro Met Ile Glu Lys Leu Pro Cys Ala
145                 150                 155                 160

Ala Leu Thr Asp Arg Glu Cys Thr Cys Pro Pro Gly Met Phe Gln Ser
                165                 170                 175

Asn Ala Thr Cys Ala Pro His Thr Val Cys Pro Val Gly Trp Gly Val
            180                 185                 190

Arg Lys Lys Gly Thr Glu Thr Glu Asp Val Arg Cys Lys Gln Cys Ala
        195                 200                 205

Arg Gly Thr Phe Ser Asp Val Pro Ser Ser Val Met Lys Cys Lys Ala
    210                 215                 220

Tyr Thr Asp Cys Leu Ser Gln Asn Leu Val Val Ile Lys Pro Gly Thr
225                 230                 235                 240

Lys Glu Thr Asp Asn Val Cys Gly Thr Leu Pro Ser Phe Ser Ser Ser
                245                 250                 255

Thr Ser Pro Ser Pro Gly Thr Ala Ile Phe Pro Arg Pro Glu His Met
            260                 265                 270

Glu Thr His Glu Val Pro Ser Ser Thr Tyr Val Pro Lys Gly Asn Leu
        275                 280                 285

Thr Ser
    290

<210> SEQ ID NO 9
<211> LENGTH: 2393
<212> TYPE: DNA
<213> ORGANISM: Mus sp.
<220> FEATURE:
<221> NAME/KEY: CDS
<222> LOCATION: (5)..(1804)
<221> NAME/KEY: misc_feature
<222> LOCATION: (1888)
<223> OTHER INFORMATION: Wherein n is a or t or c or g.

<400> SEQUENCE: 9 ggcc atg ggg acc cgg gca agc agc atc acc gcc ctc gcc tct tgc agc      49
     Met Gly Thr Arg Ala Ser Ser Ile Thr Ala Leu Ala Ser Cys Ser
     1               5                  10                  15 cgc acc gcc ggc caa gtc gga gcc acg atg gtc gcc ggc tct ctt ctc       97
Arg Thr Ala Gly Gln Val Gly Ala Thr Met Val Ala Gly Ser Leu Leu
             20                  25                  30 ctg ctt gga ttc ctc agc acc atc aca gct caa cca gaa caa aag act     145
Leu Leu Gly Phe Leu Ser Thr Ile Thr Ala Gln Pro Glu Gln Lys Thr
         35                  40                  45 ctg agt ctc cct ggc acc tac cgc cat gtt gac cgt acc act ggc cag     193
Leu Ser Leu Pro Gly Thr Tyr Arg His Val Asp Arg Thr Thr Gly Gln
     50                  55                  60 gtg cta acc tgc gac aag tgc cca gca gga acg tat gtc tcc gag cac     241
Val Leu Thr Cys Asp Lys Cys Pro Ala Gly Thr Tyr Val Ser Glu His
 65                  70                  75 tgt acc aac atg agc ctg cga gtc tgc agc agc tgc ccc gcg ggg acc     289
Cys Thr Asn Met Ser Leu Arg Val Cys Ser Ser Cys Pro Ala Gly Thr
 80                  85                  90                  95 ttt acc agg cac gag aac ggc ata gag aga tgc cat gac tgt agt cag     337
Phe Thr Arg His Glu Asn Gly Ile Glu Arg Cys His Asp Cys Ser Gln
                100                 105                 110 cca tgt cca tgg ccg atg att gag aga tta cct tgt gct gcc ttg act     385
Pro Cys Pro Trp Pro Met Ile Glu Arg Leu Pro Cys Ala Ala Leu Thr
```

```
                   115                 120                 125
gac cga gag tgc atc tgc cca cct gga atg tat cag tct aat ggt acc        433
Asp Arg Glu Cys Ile Cys Pro Pro Gly Met Tyr Gln Ser Asn Gly Thr
        130                 135                 140 tgc gct ccc cat aca gtg tgc ccc gtg ggc tgg ggt gtg cgg aag aaa        481
Cys Ala Pro His Thr Val Cys Pro Val Gly Trp Gly Val Arg Lys Lys
    145                 150                 155 ggg aca gag aat gaa gat gtg cgc tgt aag cag tgc gct cgg ggt acc        529
Gly Thr Glu Asn Glu Asp Val Arg Cys Lys Gln Cys Ala Arg Gly Thr
160                 165                 170                 175 ttc tct gac gtg cct tcc agt gtg atg aag tgt aaa gct cac acg gac        577
Phe Ser Asp Val Pro Ser Ser Val Met Lys Cys Lys Ala His Thr Asp
                180                 185                 190 tgt ctg ggt cag aac ctg gag gtg gtc aag cca ggg acc aag gag aca        625
Cys Leu Gly Gln Asn Leu Glu Val Val Lys Pro Gly Thr Lys Glu Thr
            195                 200                 205 gac aac gtc tgt ggc atg cgc ctg ttc ttc tcc agc aca aac cca cct        673
Asp Asn Val Cys Gly Met Arg Leu Phe Phe Ser Ser Thr Asn Pro Pro
        210                 215                 220 tcc tct ggc aca gtt acc ttt tct cac cct gag cat atg gaa tcc cac        721
Ser Ser Gly Thr Val Thr Phe Ser His Pro Glu His Met Glu Ser His
    225                 230                 235 gat gtc cct tcc tcc acc tat gag ccc caa ggc atg aac tca aca gat        769
Asp Val Pro Ser Ser Thr Tyr Glu Pro Gln Gly Met Asn Ser Thr Asp
240                 245                 250                 255 tcc aac tct act gcc tct gtt aga act aag gta cca agt ggc atc gag        817
Ser Asn Ser Thr Ala Ser Val Arg Thr Lys Val Pro Ser Gly Ile Glu
                260                 265                 270 gaa ggg aca gtg cct gac aat acg agc cca acc agt ggg aag gaa ggc        865
Glu Gly Thr Val Pro Asp Asn Thr Ser Pro Thr Ser Gly Lys Glu Gly
            275                 280                 285 act aat agg acc ctg cca aac cca cca caa gtt acc cac cag caa gcc        913
Thr Asn Arg Thr Leu Pro Asn Pro Pro Gln Val Thr His Gln Gln Ala
        290                 295                 300 ccc cac cac aga cac att ctg aag ctg ctg cca tcg tcc atg aag gcc        961
Pro His His Arg His Ile Leu Lys Leu Leu Pro Ser Ser Met Lys Ala
    305                 310                 315 acg ggt gag aag tcc agc aca gcc atc aag gcc ccc aag agg ggt cac        1009
Thr Gly Glu Lys Ser Ser Thr Ala Ile Lys Ala Pro Lys Arg Gly His
320                 325                 330                 335 ccc aga cag aac gct cac aag cat ttc gac atc aac gag cac ttg cct        1057
Pro Arg Gln Asn Ala His Lys His Phe Asp Ile Asn Glu His Leu Pro
                340                 345                 350 tgg atg atc gtc ctc ttc ctt ctg ctg gtc ctg gtg ctg ata gtg gtg        1105
Trp Met Ile Val Leu Phe Leu Leu Leu Val Leu Val Leu Ile Val Val
            355                 360                 365 tgc agt atc cga aag agc tcc agg act ctc aaa aag ggg ccc cgg cag        1153
Cys Ser Ile Arg Lys Ser Ser Arg Thr Leu Lys Lys Gly Pro Arg Gln
        370                 375                 380 gat ccc agc gcc ata gtg gaa aag gcg ggg ctg aag aag tcc ctg act        1201
Asp Pro Ser Ala Ile Val Glu Lys Ala Gly Leu Lys Lys Ser Leu Thr
    385                 390                 395 ccc acc cag aac cgg gag aaa tgg atc tac tac cgc aac ggc cat ggt        1249
Pro Thr Gln Asn Arg Glu Lys Trp Ile Tyr Tyr Arg Asn Gly His Gly
400                 405                 410                 415 att gac atc ttg aag ctt gta gca gcc cag gtg gga agc cag tgg aag        1297
Ile Asp Ile Leu Lys Leu Val Ala Ala Gln Val Gly Ser Gln Trp Lys
                420                 425                 430 gac atc tat cag ttt ctt tgc aac gcc agc gag agg gag gtg gcg gcc        1345
```

```
                Asp Ile Tyr Gln Phe Leu Cys Asn Ala Ser Glu Arg Glu Val Ala Ala
                            435                 440                 445 ttc tcc aat gga tac act gca gat cac gaa cgg gcc tac gcg gct ctg        1393
Phe Ser Asn Gly Tyr Thr Ala Asp His Glu Arg Ala Tyr Ala Ala Leu
            450                 455                 460 cag cac tgg acc atc cgt ggc cct gag gcc agc ctt gcc cag ctc att        1441
Gln His Trp Thr Ile Arg Gly Pro Glu Ala Ser Leu Ala Gln Leu Ile
465                 470                 475 agc gcc ttg cgc cag cac cga cgc aat gat gtt gtg gag aag att cgt        1489
Ser Ala Leu Arg Gln His Arg Arg Asn Asp Val Val Glu Lys Ile Arg
480                 485                 490                 495 ggg ctg atg gaa gac acc aca cag ttg gaa aca gac aaa ctg gct ctc        1537
Gly Leu Met Glu Asp Thr Thr Gln Leu Glu Thr Asp Lys Leu Ala Leu
                500                 505                 510 ccc atg agc ccc agt ccg ctg agc ccg agc ccc atc ccc agt cct aac        1585
Pro Met Ser Pro Ser Pro Leu Ser Pro Ser Pro Ile Pro Ser Pro Asn
            515                 520                 525 gtg aaa ctt gag aat tcc act ctc ctg aca gtg gag ccc tca ccg ctg        1633
Val Lys Leu Glu Asn Ser Thr Leu Leu Thr Val Glu Pro Ser Pro Leu
        530                 535                 540 gac aag aac aag tgc ttc ttc gtg gac gaa gtc aga gcc cct tct gcg        1681
Asp Lys Asn Lys Cys Phe Phe Val Asp Glu Val Arg Ala Pro Ser Ala
545                 550                 555 ttg cga ctc cac atc cag tgg ctc ttc agc act gag cag aaa cgg ctc        1729
Leu Arg Leu His Ile Gln Trp Leu Phe Ser Thr Glu Gln Lys Arg Leu
560                 565                 570                 575 ctt tat tac caa agg tac cca tct ctt gtg aag cct ggg gcc atc ttc        1777
Leu Tyr Tyr Gln Arg Tyr Pro Ser Leu Val Lys Pro Gly Ala Ile Phe
                580                 585                 590 ctt gac act cca cag cgc agt tgt agc tgagcccact tgaatgacct              1824
Leu Asp Thr Pro Gln Arg Ser Cys Ser
            595                 600 gttaggagac ctccaagatg aaagtgtcct caaggaagcc acatcactaa ttaacatgga      1884
tacncctaga aagtctttac aacttgtgcc ctatccagaa ccagctttga tacaggccca     1944
ttagcgtcta tccttggcat actatccaat gtgtgcttca ggagacatct gacaaaagac     2004
agtgtagctg atctggagaa ttatttccca cacttgctga gtctaaggct gaagagtgaa     2064
acccatctgg agagtcagaa gtagttttag tgtttagaat tgatcctaaa attcactcta     2124
aactagattg cacacatttt cagcatagta ggggagggggg ctagggctca gttggtaagg    2184
tgcctgccta gcaggcatga agcccagcag acacaaaaac agagtgtggt ggctctcagt    2244
tggtatttta gcatttgaga aaatatgcaa ttcaaagtca gctgggtgtg gtgggagact    2304
cctttgatcc cagcacttaa gaaagagagc tagaattcag cggccgcttt ttttacctgc    2364
ccgggcggcc gctcgagccc tatagtgag                                     2393

<210> SEQ ID NO 10
<211> LENGTH: 600
<212> TYPE: PRT
<213> ORGANISM: Mus sp.

<400> SEQUENCE: 10

Met Gly Thr Arg Ala Ser Ser Ile Thr Ala Leu Ala Ser Cys Ser Arg
1               5                   10                  15

Thr Ala Gly Gln Val Gly Ala Thr Met Val Ala Gly Ser Leu Leu Leu
            20                  25                  30

Leu Gly Phe Leu Ser Thr Ile Thr Ala Gln Pro Glu Gln Lys Thr Leu
        35                  40                  45
```

```
Ser Leu Pro Gly Thr Tyr Arg His Val Asp Arg Thr Thr Gly Gln Val
 50                  55                  60

Leu Thr Cys Asp Lys Cys Pro Ala Gly Thr Tyr Val Ser Glu His Cys
 65                  70                  75                  80

Thr Asn Met Ser Leu Arg Val Cys Ser Ser Cys Pro Ala Gly Thr Phe
                 85                  90                  95

Thr Arg His Glu Asn Gly Ile Glu Arg Cys His Asp Cys Ser Gln Pro
                100                 105                 110

Cys Pro Trp Pro Met Ile Glu Arg Leu Pro Cys Ala Ala Leu Thr Asp
            115                 120                 125

Arg Glu Cys Ile Cys Pro Gly Met Tyr Gln Ser Asn Gly Thr Cys
130                 135                 140

Ala Pro His Thr Val Cys Pro Val Gly Trp Gly Val Arg Lys Lys Gly
145                 150                 155                 160

Thr Glu Asn Glu Asp Val Arg Cys Lys Gln Cys Ala Arg Gly Thr Phe
                165                 170                 175

Ser Asp Val Pro Ser Ser Val Met Lys Cys Lys Ala His Thr Asp Cys
                180                 185                 190

Leu Gly Gln Asn Leu Glu Val Val Lys Pro Gly Thr Lys Glu Thr Asp
            195                 200                 205

Asn Val Cys Gly Met Arg Leu Phe Phe Ser Ser Thr Asn Pro Pro Ser
210                 215                 220

Ser Gly Thr Val Thr Phe Ser His Pro Glu His Met Glu Ser His Asp
225                 230                 235                 240

Val Pro Ser Ser Thr Tyr Glu Pro Gln Gly Met Asn Ser Thr Asp Ser
                245                 250                 255

Asn Ser Thr Ala Ser Val Arg Thr Lys Val Pro Ser Gly Ile Glu Glu
            260                 265                 270

Gly Thr Val Pro Asp Asn Thr Ser Pro Thr Ser Gly Lys Glu Gly Thr
            275                 280                 285

Asn Arg Thr Leu Pro Asn Pro Pro Gln Val Thr His Gln Gln Ala Pro
290                 295                 300

His His Arg His Ile Leu Lys Leu Leu Pro Ser Ser Met Lys Ala Thr
305                 310                 315                 320

Gly Glu Lys Ser Ser Thr Ala Ile Lys Ala Pro Lys Arg Gly His Pro
                325                 330                 335

Arg Gln Asn Ala His Lys His Phe Asp Ile Asn Glu His Leu Pro Trp
            340                 345                 350

Met Ile Val Leu Phe Leu Leu Val Leu Val Leu Ile Val Val Cys
            355                 360                 365

Ser Ile Arg Lys Ser Ser Arg Thr Leu Lys Lys Gly Pro Arg Gln Asp
370                 375                 380

Pro Ser Ala Ile Val Glu Lys Ala Gly Leu Lys Lys Ser Leu Thr Pro
385                 390                 395                 400

Thr Gln Asn Arg Glu Lys Trp Ile Tyr Tyr Arg Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
            435                 440                 445

Ser Asn Gly Tyr Thr Ala Asp His Glu Arg Ala Tyr Ala Ala Leu Gln
450                 455                 460
```

```
His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Val
        515                 520                 525

Lys Leu Glu Asn Ser Thr Leu Leu Thr Val Glu Pro Ser Pro Leu Asp
    530                 535                 540

Lys Asn Lys Cys Phe Phe Val Asp Glu Val Arg Ala Pro Ser Ala Leu
545                 550                 555                 560

Arg Leu His Ile Gln Trp Leu Phe Ser Thr Glu Gln Lys Arg Leu Leu
                565                 570                 575

Tyr Tyr Gln Arg Tyr Pro Ser Leu Val Lys Pro Gly Ala Ile Phe Leu
                580                 585                 590

Asp Thr Pro Gln Arg Ser Cys Ser
                595                 600

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 11
actggatccc cggttcagcc atgggg                                    26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: (1)
<223> OTHER INFORMATION: wherein any n is an a, t, c or g

<400> SEQUENCE: 12
gtcctcgagt gaggttaagt tacctttggg                                30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 13
ccgctcgagt gagcccaaat cttgtgacaa a                              31

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 14
gctctagact tttacccggg gacagggag                                 29
```

```
<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 15
aattctgcag cgaaaacctg tattttcagg gt                            32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 16
tcgaaccctg aaaatacagg ttttcgctgc ag                            32

<210> SEQ ID NO 17
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 17
ggatccattt aggtgacact atagaagccc agtcacgacg ttgtaaaacg acggc   55

<210> SEQ ID NO 18
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 18
cggccgaatt accctcacta aagggacgga taacaatttc acacaggaaa cagc    54

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 19
ttccatcagc ccacgaatct tctccac                                  27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 20
ctccacaaca tcattgcgtc ggtgctg                                  27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: primer
```

-continued

```
<400> SEQUENCE: 21
cattctctgt cccttcttc cgcacac                                              27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 22
gactgataca ttccaggtgg gcagatg                                             27

<210> SEQ ID NO 23
<211> LENGTH: 36
<212> TYPE: PRT
<213> ORGANISM: Homo sapiens

<400> SEQUENCE: 23

Met Gly Ser Arg Pro Gly Gly Gly Gly Cys Gly Ala Gly Gln Lys
  1               5                  10                  15

Gln Pro Pro Ile Pro Ala Ala Pro Arg Ala Pro Ala Thr Leu Arg Val
                 20                  25                  30

Pro Gly Ser Ala
         35

<210> SEQ ID NO 24
<211> LENGTH: 158
<212> TYPE: PRT
<213> ORGANISM: Homo sapiens

<400> SEQUENCE: 24

Tyr Leu His Tyr Asp Glu Glu Thr Ser His Gln Leu Leu Cys Asp Lys
  1               5                  10                  15

Cys Pro Pro Gly Thr Tyr Leu Lys Gln His Cys Thr Ala Lys Trp Lys
                 20                  25                  30

Thr Val Cys Ala Pro Cys Pro Asp His Tyr Tyr Thr Asp Ser Trp His
         35                  40                  45

Thr Ser Asp Glu Cys Leu Tyr Cys Ser Pro Val Cys Lys Glu Leu Gln
     50                  55                  60

Tyr Val Lys Gln Glu Cys Asn Arg Thr His Asn Arg Val Cys Glu Cys
 65                  70                  75                  80

Lys Glu Gly Arg Tyr Leu Glu Ile Glu Phe Cys Leu Lys His Arg Ser
                 85                  90                  95

Cys Pro Pro Gly Phe Gly Val Val Gln Ala Gly Thr Pro Glu Arg Asn
                100                 105                 110

Thr Val Cys Lys Arg Cys Pro Asp Gly Phe Phe Ser Asn Glu Thr Ser
            115                 120                 125

Ser Lys Ala Pro Cys Arg Lys His Thr Asn Cys Ser Val Phe Gly Leu
        130                 135                 140

Leu Leu Thr Gln Lys Gly Asn Ala Thr His Asp Asn Ile Cys
145                 150                 155

<210> SEQ ID NO 25
<211> LENGTH: 189
<212> TYPE: PRT
<213> ORGANISM: Homo sapiens

<400> SEQUENCE: 25
```

-continued

```
Thr Ala Gln Met Cys Cys Ser Lys Cys Ser Pro Gly Gln His Ala Lys
 1               5                  10                 15

Val Phe Cys Thr Lys Thr Ser Asp Thr Val Cys Asp Ser Cys Glu Asp
            20                  25                  30

Ser Thr Tyr Thr Gln Leu Trp Asn Trp Val Pro Glu Cys Leu Ser Cys
            35                  40                  45

Gly Ser Arg Cys Ser Ser Asp Gln Val Glu Thr Gln Ala Cys Thr Arg
        50                  55                  60

Glu Gln Asn Arg Ile Cys Thr Cys Arg Pro Gly Trp Tyr Cys Ala Leu
 65                  70                  75                  80

Ser Lys Gln Glu Gly Cys Arg Leu Cys Ala Pro Leu Arg Lys Cys Arg
                85                  90                  95

Pro Gly Phe Gly Val Ala Arg Pro Gly Thr Glu Thr Ser Asp Val Val
            100                 105                 110

Cys Lys Pro Cys Ala Pro Gly Thr Phe Ser Asn Thr Thr Ser Ser Thr
            115                 120                 125

Asp Ile Cys Arg Pro His Gln Ile Cys Asn Val Val Ala Ile Pro Gly
            130                 135                 140

Asn Ala Ser Met Asp Ala Val Cys Thr Ser Thr Ser Pro Thr Arg Ser
145                 150                 155                 160

Met Ala Pro Gly Ala Val His Leu Pro Gln Pro Val Ser Thr Arg Ser
            165                 170                 175

Gln His Thr Gln Pro Thr Pro Glu Pro Ser Thr Ala Pro
            180                 185
```

NUCLEIC ACIDS ENCODING OSTEOPROTEGERN-LIKE PROTEINS AND METHODS OF USING SAME

RELATED APPLICATIONS

This patent application claims priority to U.S. Ser. No. 60/105,481, filed Oct. 23, 1998, and U.S. Ser. No. 60/156,993, filed Oct. 1, 1999, which are incorporated herein by reference in their entirety.

FIELD OF THE INVENTION

The invention relates in general to nucleic acids and proteins and in particular to nucleic acids and their encoded polypeptides involved in metabolic bone diseases, such as osteoporosis or osteopetrosis.

BACKGROUND OF THE INVENTION

Bone is a highly dynamic tissue characterized by continuous formation and readsorption. An imbalance in formation and readsorption can be implicated in metabolic bone diseases such as osteopetrosis and osteoporosis.

Bone formation and readsorption is mediated at least in part by osteoblasts and osteoclasts. These cells exert opposite effects on bone growth. Osteoblasts secrete molecules that form the organic matrix of bone, while osteoclasts promote dissolution of the bone matrix and solubilization of bone salts. Net bone tissue formation occurs when the rate of bone deposition exceeds the rate of bone resorption, while bone loss occurs when the rate of resorption exceeds deposition. Increased breakdown of bone, as is observed in diseases such as osteoporosis, can lead to reduced bone mass and strength, as well as an increased risk of fractures, and slow or incomplete repair of broken bones.

Osteoclasts are thought to form from hematopoietic precursor cells in the bone marrow. Early development of bone marrow precursor cells to preosteoclasts are believed to mediated by soluble factors such as tumor necrosis factor-alpha. (TNF-alpha), tumor necrosis factor-beta (TNF-beta), interleukin-1 (IL-1), interleukin-4 (IL-4), interleukin-6 (IL-6), and leukemia inhibitory factor (LIF).

One protein involved in bone metabolism is osteoprotegerin (OPG), which is also known as osteoclastogenesis inhibitory factor (OCIF). OPG includes two polypeptide domains having different structural and functional properties. It has cytokine-like activities and is a member of the tumor necrosis factor (TNF) receptor superfamily. OPG has been reported to act as a soluble factor in the regulation of bone mass by negatively regulating osteoclast formation in vitro and in vivo. By inhibiting osteoclast formation, OPG is thought to promote net bone growth. Transgenic mice expressing the OPG polypeptide show increased bone density and lowered amounts of bone loss.

OPG-deficient mice also exhibit medial calcification of the aorta and renal arteries, suggesting that regulation of OPG, its signaling pathway, or its ligand(s) may play a role in the long-observed association between osteoporosis and vascular calcification.

SUMMARY OF THE INVENTION

The invention is based in part on the discovery of novel nucleic acids encoding osteoprotegerin-like (OPGx) polypeptides. The OPGx polypeptides and nucleic acids are useful, inter alia, for treating disorders associated with bone metabolism.

Accordingly, in one aspect the invention features an OPGx nucleic acid. In some embodiments, the OPGx nucleic acid encodes a polypeptide that is not longer than 650 amino acids. In other embodiments, the OPGx nucleic acid encodes a polypeptide that is not longer than 600, 550, 500, 450, 400, 375, 325, 300, or even 295 amino acids.

The invention also features OPGx polypeptides. In some embodiments, the OPGx polypeptide is not longer than 650 amino acids. In other embodiments, the OPGx polypeptide is not longer than 600, 550, 500, 450, 400, 375, 325, 300, or even 295 amino acids.

Also included in the invention are antibodies to OPGx polypeptides. In some embodiments, the antibodies are monoclonal antibodies.

In other aspects, the invention features pharmaceutical compositions including an OPGx nucleic acid, pharmaceutical compositions including an OPGx polypeptide, and pharmaceutical compositions including an antibody to an OPGx polypeptide.

Also included in the invention is a method of promoting bone growth by administering to a patient in need thereof an effective amount of an OPGx polypeptide, an OPGx polypeptide agonist, or an OPGx nucleic acid.

The invention further includes a method of inhibiting osteoclast-mediated bone resorption by administering to a subject in need thereof an effective amount of an OPGx polypeptide, an OPGx agonist, or an OPGx nucleic acid.

The patient can be, e.g., a human or a non-human mammal such as a dog, cat, horse, cow, sheep, or goat. The patient can suffers from, e.g., osteoporosis, osteopetrosis, or another condition characterized by loss of bone, breakdown of bone tissue, or excessive readsorption of bone tissue.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

Other features and advantages of the invention will be apparent from the following detailed description and claims.

BRIEF DESCRIPTION OF THE FIGURES

FIG. 1 illustrates the nucleic acid (SEQ ID NO:1) and translated amino acid (SEQ ID NO:2) residue sequences of a human OPGx1 protein.

FIGS. 2A and 2B illustrates the nucleic acid (SEQ ID NO:3) and translated amino acid (SEQ ID NO:4) residue sequences of a human OPGx2 protein.

FIG. 3 illustrates a sequence comparison of a portion of the OPGx polypeptide (Query) with a related sequence from human osteoprotegerin protein having 401 amino acid residues (Sbjct). Residue numbers shown are relative.

FIG. 4 illustrates a sequence comparison of a portion of the OPGx polypeptide (Query) with a related sequence from human tissue necrosis factor (TNF) receptor having 425 amino acid residues (Sbjct). Residue numbers shown are relative.

FIG. 5 illustrates the nucleic acid (SEQ ID NO:5) and translated amino acid (SEQ ID NO:6) residue sequence of a human OPGx3 protein.

FIGS. 6A and 6B illustrates the nucleic acid (SEQ ID NO:7) and translated amino acid (SEQ ID NO:8) residue sequences of a human OPGx4 protein.

FIG. 7 shows Western blots of SDS PAGE experiments on the product obtained when hOPGx protein is secreted by 293 cells (Panel A), and by SF9 cells (Panel B).

FIG. 8 shows SDS-PAGE and silver staining analysis of 250 ng of purified OPGx-Ig protein.

FIGS. 9A and 9B illustrate the nucleic acid (SEQ ID NO:9) and translated amino acid (SEQ ID NO:10) residue sequences of a murine OPGx5 protein.

DETAILED DESCRIPTION OF THE INVENTION

Disclosed herein are nucleic acids encoding osteoprotegerin-like polypeptide sequences (OPGx) and their polypeptide products. The nucleotide sequences of these OPGx sequences, along with their encoded polypeptides, are shown in FIGS. 1, 2, 5 6, and 9. FIG. 1 illustrates the sequence of OPGX1, which includes a 1686 nucleic acid sequence (SEQ ID NO:1) along with an encoded polypeptide of 290 amino acids (SEQ ID NO:2).

FIG. 2 illustrates the sequence of OPGX2, which includes a nucleic acid sequence of 2271 nucleotides (SEQ ID NO:3), along with an encoded polypeptide of 691 amino acids (SEQ ID NO:4).

The 773 nucleic acid sequence of OPGX3 (SEQ ID NO:5), along with an encoded polypeptide of 254 amino acids (SEQ ID NO:6), is shown in FIG. 5. FIG. 6 illustrates the sequence of OPGX4, which includes a nucleic acid sequence of 1686 nucleotides and an encoded polypeptide of 190 amino acids. FIG. 9 shows the 2314 nucleotide sequence of OPGX5 (SEQ ID NO:9), along with an encoded polypeptide of 600 amino acids. The OPGX1–4 sequences shown are of human origin, while the OPGX5 sequence is of murine origin.

OPGX1, OPGX2, and OPGX4 contain a 36 amino acid extension (SEQ ID NO:23) at their amino terminus relative to the DR6 TNF-related death receptor amino acid sequence (Accession AF068868.1). Expression ofthe OPGx proteins is found in bone, lymph node, germinal B cells and kidney. In addition, there appears to be at least two splice variants of this gene, a transmembrane form and a extracellular domain form (compare FIGS. 2 and 9 with FIGS. 1, 5 and 6).

The amino acid sequences of OPGX1, OPGX3, and OPGX4 (SEQ ID NOS:2, 6, and 8) terminate just before the TNF receptor family transmembranal domain. This structural motif indicates at least some OPGx proteins may be secreted. Hydropathy and signal peptide analyses also indicate that some OPGx proteins may be secreted. Structural motif computer programs have identified a TNF receptor-like structural "signature." Additionally, cysteine amino acid residue alignment within the TNF receptor and the osteoprotegerin-like protein of the present invention show the cysteines of TNF receptor and OPGx can be aligned in at least some of the OPGx proteins of the invention.

The OPGx proteins are useful, inter alia, in modulating bone formation, osteoporosis, anti-inflammation and in modulating cell death, e.g., inducing apoptotic pathways by administering OPGx polypeptides, OPGx nucleic acids, or OPGx agonists, or inhibiting apoptotic pathways by administering OPGx antagonists. Members of the TNF receptor and ligand super-families play an important role in the regulation of numerous biological processes including, but not limited to: cytokine production, apoptosis, cell activation, lymphocyte co-stimulation, immunoglobulin secretion and immunoglobulin isotype switching.

The OPGx proteins inhibiting osteoclast-mediated bone reabsorption in a subject that is suspected of experiencing osteoclast-mediated bone reabsorption or is at risk of developing osteoclast-mediated bone reabsorption, as well as treating a subject that is suffering from a decrease in bone mass or is at risk of undergoing a decrease in bone mass. As is discussed in detail below, the methods include administering an amount the polypeptides or polynucleotides of the invention in amounts, and for durations of time, that are effective to inhibit reabsorption in the subject, or that are effective to treat the subject. The appropriate amounts and durations to be administered, or that are used in the treatments, may be assessed or evaluated by studying subjects undergoing such administering or such treatments. Practitioners skilled in the veterinarian (in the case of nonhuman subjects) and medical (in the case of human subjects) specialties such as orthopedics, radiology, and geriatric gynecology have sufficient training to evaluate the effectiveness of such methods. Techniques employed to assess the efficacy of treatment include any procedures or diagnostic methods capable of assessing bone density and/or bone mass, for example, and include, by way of nonlimiting example, various radiological procedures such as x-ray imaging and tomography, bone-specific radioisotope imaging, magnetic resonance imaging, and ultrasonography. A treatment may be considered effective by a variety of criteria, including but not limited to reversing an actual decrease in bone mass, achieving a steady level or extent of bone mass, and regeneration of depleted bone mass.

OPGx Nucleic Acids

One aspect of the invention pertains to isolated nucleic acid molecules that encode OPGx proteins or biologically active portions thereof, as well as nucleic acid fragments sufficient for use as hybridization probes to identify OPGx-encoding nucleic acids (e.g., OPGx mRNA) and fragments for use as PCR primers for the amplification or mutation of OPGx nucleic acid molecules. The nucleic acid may encode a polypeptide which includes the amino acid sequence MetGlySerArgProGlyGlyGlyGlyGlyCysGlyAlaGlyGln-LysGlnProProIleProAlaAlaProArgAla ProAlaThr-LeuArgValProGlySerAla (SEQ ID NO:23), or a polypeptide having one or more conservative amino acid substitutions within this sequence. The remainder of the nucleic acid may hybridize to one or more of the remaining regions of an OPGx nucleic acid described herein, as discussed below. Alternatively, the nucleic acid may encode a polypeptide comprising SEQ ID NO:23, or with one or more conservative amino substitutions therein.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated OPGx nucleic acid molecule can contain less than about 5 kb, 4 kb, 3 kb, 2 kb, 1 kb, 0.5 kb, 0.1 or 0.01 kb of nucleotide sequences that naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NOs: 1, 3, 5, 7 or 9, or a complement of any of these nucleotide sequences, can be isolated using standard molecular biology techniques and the sequence information provided herein. Using all or a portion of the nucleic acid sequences of SEQ ID NOs: 1, 3, 5, 7 or 9 as a hybridization probe, OPGx nucleic acid molecules can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to OPGx nucleotide sequences can be prepared by standard synthetic techniques, e.g., using an automated DNA synthesizer.

In another embodiment, an isolated nucleic acid molecule of the invention comprises a nucleic acid molecule that is a complement of the nucleotide sequence shown in SEQ ID NOs: 1, 3, 5, 7 or 9. In another embodiment, an isolated nucleic acid molecule of the invention comprises a nucleic acid molecule that is a complement of the nucleotide sequence shown in, or a portion of this nucleotide sequence. A nucleic acid molecule that is complementary to the nucleotide sequence shown in SEQ ID NOs: 1, 3, 5, 7 or 9 is one that is sufficiently complementary to the nucleotide sequence shown in SEQ ID NOs: 1, 3, 5, 7 or 9 that it can hydrogen bond with little or no mismatches to the nucleotide sequence shown in SEQ ID NOs: 1, 3, 5, 7 or 9, thereby forming a stable duplex.

Moreover, the nucleic acid molecule of the invention can comprise only a portion of the nucleic acid sequence of SEQ ID NOs: 1, 3, 5, 7 or 9, e.g., a fragment that can be used as a probe or primer or a fragment encoding a biologically active portion of OPGx. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding these proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

The nucleotide sequence determined from the cloning of the human OPGx gene allows for the generation of probes and primers designed for use in identifying and/or cloning OPGx homologues in other cell types, e.g., from other tissues, as well as OPGx homologues from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NOs: 1, 3, 5, 7 or 9; or an anti-sense strand nucleotide sequence of SEQ ID NOs: 1, 3, 5, 7 or 9; or of a naturally occurring mutant of SEQ ID NOs: 1, 3, 5, 7 or 9.

Probes based on the human OPGx nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a OPGx protein, such as by measuring a level of a OPGx-encoding nucleic acid in a sample of cells from a subject e.g., detecting OPGx mRNA levels or determining whether a genomic OPGx gene has been mutated or deleted.

"A polypeptide having a biologically active portion of OPGx" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of OPGx" can be prepared by isolating a portion of SEQ ID NOs: 1, 3, 5, 7 or 9, that encodes a polypeptide having a OPGx biological activity (the biological activities of the OPGx proteins are described below), expressing the encoded portion of OPGx protein (e.g., by recombinant expression in vitro) and assessing the activity of the encoded portion of OPGx.

Also included in the invention are nucleic acids encoding polypeptides having one or more OPGx activities. These include, e.g., (i) binding to the cytotoxic ligand TRAIL (Emery, et al., J Biol Chem. 1998):14363–7, and (ii) binding to the osteoprotegerin ligand (Lacey D L, et al., Cell. 1998 April 17;93(2):165–76).

OPGx variants

The invention further encompasses nucleic acid molecules that differ from the nucleotide sequence shown in SEQ ID NOs: 1, 3, 5, 7 or 9, due to degeneracy of the genetic code and thus encode the same OPGx protein as that encoded by the nucleotide sequence shown in SEQ ID NOs: 1, 3, 5, 7 or 9. In another embodiment, an isolated nucleic acid molecule of the invention has a nucleotide sequence encoding a protein having an amino acid sequence shown in SEQ ID NOs. 2, 4, 6, 8 or 10.

In addition to the human OPGx nucleotide sequences shown in SEQ ID NO: 1, 3, 5, or 7, it will be appreciated by those skilled in the art that DNA sequence polymorphisms that lead to changes in the amino acid sequences of OPGx may exist within a population (e.g., the human population). Such genetic polymorphism in the OPGx gene may exist among individuals within a population due to natural allelic variation. As used herein, the terms "gene" and "recombinant gene" refer to nucleic acid molecules comprising an open reading frame encoding a OPGx protein, preferably a mammalian OPGx protein. Such natural allelic variations can typically result in 1–5% variance in the nucleotide sequence of the OPGx gene. Any and all such nucleotide variations and resulting amino acid polymorphisms in OPGx that are the result of natural allelic variation and that do not alter the functional activity of OPGx are intended to be within the scope of the invention.

Moreover, nucleic acid molecules encoding OPGx proteins from other species, and thus that have a nucleotide sequence that differs from the sequence of SEQ ID NOs: 1, 3, 5, 7 or 9, are intended to be within the scope of the invention. Nucleic acid molecules corresponding to natural allelic variants and homologues of the OPGx cDNAs of the invention can be isolated based on their homology to the human or murine OPGx nucleic acids disclosed herein using the human or murine sequences, or a portion thereof, as a hybridization probe according to standard hybridization techniques under stringent hybridization conditions. For example, a soluble human OPGx cDNA can be isolated based on its homology to human membrane-bound OPGx. Likewise, a membrane-bound human OPGx cDNA can be isolated based on its homology to soluble human OPGx.

In another embodiment, an isolated nucleic acid molecule of the invention is at least 6 nucleotides in length and hybridizes under stringent conditions to the nucleic acid molecule comprising the nucleotide sequence of SEQ ID NOs: 1, 3, 5, 7 or 9. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding OPGx proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequence of SEQ ID NOs: 1, 3, 5, 7 or 9 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOs: 1, 3, 5, 7 or 9, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NOs: 1, 3, 5, 7 or 9, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition to naturally-occurring allelic variants of the OPGx sequence that may exist in the population, the skilled artisan will further appreciate that changes can be introduced by mutation into the nucleotide sequence of SEQ ID NOs: 1, 3, 5, 7 or 9, thereby leading to changes in the amino acid sequence of the encoded OPGx protein, without altering the functional ability of the OPGx protein. For example, nucleotide substitutions leading to amino acid substitutions at "non-essential" amino acid residues can be made in the sequence of SEQ ID NOs: 1, 3, 5, 7 or 9. A "non-essential" amino acid residue is a residue that can be altered from the wild-type sequence of OPGx without altering the biological activity, whereas an "essential" amino acid residue is required for biological activity. For example, amino acid residues that are conserved among the OPGx proteins of the present invention, are predicted to be particularly unamenable to alteration.

Another aspect of the invention pertains to nucleic acid molecules encoding OPGx proteins that contain changes in amino acid residues that are not essential for activity. Such OPGx proteins differ in amino acid sequence from SEQ ID NOs: 2, 4, 6, 8 or 10, yet retain biological activity. In one embodiment, the isolated nucleic acid molecule comprises a nucleotide sequence encoding a protein, wherein the protein comprises an amino acid sequence at least about 45% homologous to the amino acid sequence of SEQ ID NO:2, 4, 6, 8, of 10. Preferably, the protein encoded by the nucleic acid molecule is at least about 60% homologous to SEQ ID NOs: 2, 4, 6, 8 or 10, more preferably at least about 70% homologous to SEQ ID NO:2, 4, 6, 8 or 10, still more preferably at least about 80% homologous to SEQ ID NO:2, 4, 6, 8 or 10, even more preferably at least about 90% homologous to SEQ ID NO:2, 4, 6, 8 or 10, and most preferably at least about 95% homologous to SEQ ID NO:2, 4, 6, 8 or 10.

An isolated nucleic acid molecule encoding a OPGx protein homologous to the protein of SEQ ID NOs:2, 4, 6, 8 or 10 can be created by introducing one or more nucleotide substitutions, additions or deletions into the nucleotide sequence of SEQ ID NOs: 1, 3, 5, 7 or 9, such that one or more amino acid substitutions, additions or deletions are introduced into the encoded protein.

Mutations can be introduced into SEQ ID NOs: 1, 3, 5, 7 or 9 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in OPGx is replaced with another amino acid residue from the same side chain family. Alternatively, in another embodiment, mutations can be introduced randomly along all or part of a OPGx coding sequence, such as by saturation mutagenesis, and the resultant mutants can be screened for OPGx biological activity to identify mutants that retain activity. Following mutagenesis of SEQ ID NOs: 1, 3, 5, 7 or 9, the encoded protein can be expressed by any recombinant technology known in the art and the activity of the protein can be determined.

In one embodiment, a mutant OPGx protein can be assayed for (1) the ability to form protein: protein interactions with other OPGx proteins, other cell-surface proteins, or biologically active portions thereof, (2) complex formation between a mutant OPGx protein and a OPGx ligand; (3) the ability of a mutant OPGx protein to bind to an intracellular target protein or biologically active portion thereof; (e.g. avidin proteins).

In yet another embodiment, a mutant OPGx can be assayed for the ability to perform TNF receptor super family member activities, such as, (i) complex formation between a OPGx protein and an osteoprotegerin ligand protein, as described in and (ii) interaction of a OPGx protein with other proteins. In yet another embodiment, a OPGx activity is at least one or more of the following activities: (i) modulation of TNF superfamily-related protein activity; and (ii) regulation of apoptosis, e.g., induction of apoptosis.

Antisense

Another aspect of the invention pertains to isolated antisense nucleic acid molecules that are hybridizable to or complementary to the nucleic acid molecule comprising the nucleotide sequence of SEQ ID NOs: 1, 3, 5, 7 or 9, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire OPGx coding strand, or to only a portion thereof. Nucleic acid molecules encoding fragments, homologs, derivatives and analogs of a OPGx protein of SEQ ID NOs: 1, 3, 5, 7 or 9, or antisense nucleic acids complementary to a OPGx nucleic acid sequence of SEQ ID NOs: 1, 3, 5, 7 or 9, are additionally provided.

In one embodiment, an antisense nucleic acid molecule is antisense to a "coding region" of the coding strand of a nucleotide sequence encoding OPGx. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding OPGx. The term "noncoding region" refers to 5' and 3' sequences which flank the coding region that are not translated into amino acids (i.e., also referred to as 5' and 3' untranslated regions).

Given the coding strand sequences encoding OPGx disclosed herein (e.g., SEQ ID NOs: 1, 3, 5, 7 or 9), antisense nucleic acids of the invention can be designed according to the rules of Watson and Crick or Hoogsteen base pairing. The antisense nucleic acid molecule can be complementary to the entire coding region of OPGx mRNA, but more preferably is an oligonucleotide that is antisense to only a portion of the coding or noncoding region of OPGx mRNA. For example, the antisense oligonucleotide can be complementary to the region surrounding the translation start site of OPGx mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a OPGx protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res 15: 6625–6641). The antisense nucleic acid molecule can also comprise a 2'-o-methylribonucleotide (Inoue et al. (1987) Nucleic Acids Res 15: 6131–6148) or a chimeric RNA-DNA analogue (Inoue et al. (1987) FEBS Lett 215: 327–330).

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave OPGx mRNA transcripts to thereby inhibit translation of OPGx mRNA. A ribozyme having specificity for a OPGx-encoding nucleic acid can be designed based upon the nucleotide sequence of a OPGx cDNA disclosed herein (i.e., SEQ ID NOs: 1, 3, 5, 7 or 9). For example, a derivative of a Tetrahymena L-19 IVS RNA can be constructed in which the nucleotide sequence of the active site is complementary to the nucleotide sequence to be cleaved in a OPGx-encoding mRNA. See, e.g., Cech et al. U.S. Pat. No. 4,987,071; and Cech et al. U.S. Pat. No. 5,116,742. Alternatively, OPGx mRNA can be used to select a catalytic RNA having a specific ribonuclease activity from a pool of RNA molecules. See, e.g., Bartel et al., (1993) Science 261:1411–1418.

Alternatively, OPGx gene expression can be inhibited by targeting nucleotide sequences complementary to the regulatory region of the OPGx (e.g., the OPGx promoter and/or enhancers) to form triple helical structures that prevent transcription of the OPGx gene in target cells. See generally, Helene. (1991) Anticancer Drug Des. 6: 569–84; Helene. et al. (1992) Ann. N.Y. Acad. Sci. 660:27–36; and Maher (1992) Bioassays 14: 807–15.

In various embodiments, the nucleic acids of OPGx can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorg Med Chem 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) PNAS 93: 14670–675.

PNAs of OPGx can be used in therapeutic and diagnostic applications. For example, PNAs can be used as antisense or antigene agents for sequence-specific modulation of gene expression by, e.g., inducing transcription or translation arrest or inhibiting replication. PNAs of OPGx can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of OPGx can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of OPGx can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) Nucl Acids Res 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) Nucl Acid Res 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) Bioorg Med Chem Lett 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. W088/09810) or the blood-brain barrier (see, e.g., PCT Publication No. W089/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

OPGx Proteins

One aspect of the invention pertains to isolated OPGx proteins, and biologically active portions thereof, or derivatives, fragments, analogs or homologs thereof. Also provided are polypeptide fragments suitable for use as immunogens to raise anti-OPGx antibodies. In one embodiment, native OPGx proteins can be isolated from cells or tissue sources by an appropriate purification scheme using standard protein purification techniques. In another embodiment, OPGx proteins are produced by recombinant DNA techniques. Alternative to recombinant expression, a OPGx protein or polypeptide can be synthesized chemically using standard peptide synthesis techniques.

An "isolated" or "purified" protein or biologically active portion thereof is substantially free of cellular material or other contaminating proteins from the cell or tissue source from which the OPGx protein is derived, or substantially free from chemical precursors or other chemicals when chemically synthesized. The language "substantially free of cellular material" includes preparations of OPGx protein in which the protein is separated from cellular components of the cells from which it is isolated or recombinantly produced. In one embodiment, the language "substantially free of cellular material" includes preparations of OPGx protein having less than about 30% (by dry weight) of non-OPGx protein (also referred to herein as a "contaminating protein"), more preferably less than about 20% of non-OPGx protein, still more preferably less than about 10% of non-OPGx protein, and most preferably less than about 5% non-OPGx protein. When the OPGx protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of OPGx protein in which the protein is separated from chemical precursors or other chemicals that are involved in the synthesis of the protein. In one embodiment, the language "substantially free of chemical precursors or other chemicals" includes preparations of OPGx protein having less than about 30% (by dry weight) of chemical precursors or non-OPGx chemicals, more preferably less than about 20% chemical precursors or non-OPGx chemicals, still more preferably less than about 10% chemical precursors or non-OPGx chemicals, and most preferably less than about 5% chemical precursors or non-OPGx chemicals.

Biologically active portions of a OPGx protein include peptides comprising amino acid sequences sufficiently homologous to or derived from the amino acid sequence of the OPGx protein, e.g., the amino acid sequence shown in SEQ ID NOs: 2, 4, 6, 8 or 10, that include fewer amino acids than the full length OPGx proteins, and exhibit at least one activity of a OPGx protein. Typically, biologically active portions comprise a domain or motif with at least one activity of the OPGx protein. A biologically active portion of a OPGx protein can be a polypeptide which is, for example, 10, 25, 50, 100 or more amino acids in length.

Moreover, other biologically active portions, in which other regions of the protein are deleted, can be prepared by recombinant techniques and evaluated for one or more of the functional activities of a native OPGx protein.

In some embodiments, the OPGx protein has an amino acid sequence shown in SEQ ID NOs:2, 4, 6, 8 or 10. In other embodiments, the OPGx protein is substantially homologous to SEQ ID NOs: 2, 4, 6, 8 or 10 and retains the functional activity of the protein of SEQ ID NOs: 2, 4, 6, 8 or 10, yet differs in amino acid sequence due to natural allelic variation or mutagenesis, as described in detail below. Accordingly, in another embodiment, the OPGx protein is a protein that comprises an amino acid sequence at least about 45% homologous to the amino acid sequence of SEQ ID NO:2, 4, 6, 8 or 10 and retains the finctional activity of the OPGx proteins having these amino acid sequences.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOs: 1, 3, 5, 7 or 9.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides OPGx chimeric or fusion proteins. As used herein, a OPGx "chimeric protein" or "fusion protein" comprises a OPGx polypeptide operatively linked to a non-OPGx polypeptide. A "OPGx polypeptide" refers to a polypeptide having an amino acid sequence corresponding to OPGx, whereas a "non-OPGx polypeptide" refers to a polypeptide having an amino acid sequence corresponding to a protein that is not substantially homologous to the OPGx protein, e.g., a protein that is different from the OPGx protein and that is derived from the same or a different organism. Within a OPGx fusion protein the OPGx polypeptide can correspond to all or a portion of a OPGx protein. In one embodiment, a OPGx fusion protein comprises at least one biologically active portion of a OPGx protein. In another embodiment, a OPGx fusion protein comprises at least two biologically active portions of a OPGx protein. In yet another embodiment, a OPGx fusion protein comprises at least three biologically active portions of a OPGx protein. Within the fusion protein, the term "operatively linked" is intended to indicate that the OPGx polypeptide and the non-OPGx polypeptide are fused in-frame to each other. The non-OPGx polypeptide can be fused to the N-terminus or C-terminus of the OPGx polypeptide.

For example, in one embodiment a OPGx fusion protein comprises a OPGx domain operably linked to the extracellular domain of a second protein. Such fusion proteins can be further utilized in screening assays for compounds which modulate OPGx activity (such assays are described in detail below).

In yet another embodiment, the fusion protein is a GST-OPGx fusion protein in which the OPGx sequences are fused to the C-terminus of the GST (i.e., glutathione S-transferase) sequences. Such fusion proteins can facilitate the purification of recombinant OPGx.

In another embodiment, the fusion protein is a OPGx protein containing a heterologous signal sequence at its N-terminus. In certain host cells (e.g., mammalian host cells), expression and/or secretion of OPGx can be increased through use of a heterologous signal sequence.

A OPGx chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A OPGx-encoding nucleic acid can be cloned into such an expression vector such that the fusion moiety is linked in-frame to the OPGx protein.

Anti-OPGx Antibodies

An isolated OPGx protein, or a portion or fragment thereof, can be used as an immunogen to generate antibodies that bind OPGx using standard techniques for polyclonal and monoclonal antibody preparation. The full-length OPGx protein can be used or, alternatively, the invention provides antigenic peptide fragments of OPGx for use as immunogens. The antigenic peptide of OPGx comprises at least 8 amino acid residues of the amino acid sequence shown in SEQ ID NOs:2, 4, 6, 8 or 10 and encompasses an epitope of OPGx such that an antibody raised against the peptide forms a specific immune complex with OPGx. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of OPGx that are located on the surface of the protein, e.g., hydrophilic regions.

As disclosed herein, OPGx protein sequence of SEQ ID NOs: 2, 4, 6, 8 or 10, or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as OPGx. Such antibodies include, but are not limited to, polyclonal, monoclonal, chimeric, single chain, $F_{ab}$ and $F_{(ab')2}$ fragments, and an $F_{ab}$ expression library. In a specific embodiment, antibodies to human OPGx proteins are disclosed. Various procedures known within the art may be used for the production of polyclonal or monoclonal antibodies to a OPGx protein sequence of SEQ ID NOs: 2, 4, 6, 8 or 10, or derivatives, fragments, analogs or homologs thereof.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed OPGx protein or a chemically synthesized OPGx polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against OPGx can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of OPGx. A monoclonal antibody composition thus typically displays a single binding affinity for a particular OPGx protein with which it immunoreacts. For preparation of monoclonal antibodies directed towards a particular OPGx protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 *Nature* 256: 495–497); the trioma technique; the human B-cell hybridoma technique (see Kozbor, et al., 1983 *Immunol Today* 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. *Proc Natl Acad Sci USA* 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

According to the invention, techniques can be adapted for the production of single-chain antibodies specific to a OPGx protein (see e.g., U.S. Pat. No. 4,946,778). In addition, methods can be adapted for the construction of $F_{ab}$ expression libraries (see e.g., Huse, et al., 1989 *Science* 246: 1275–1281) to allow rapid and effective identification of monoclonal $F_{ab}$ fragments with the desired specificity for a OPGx protein or derivatives, fragments, analogs or homologs thereof. Non-human antibodies can be "humanized" by techniques well known in the art. See e.g., U.S. Pat. No. 5,225,539. Antibody fragments that contain the idiotypes to a OPGx protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-OPGx antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al.(1988) *Science* 240:1041–1043; Liu et al. (1987) *PNAS* 84:3439–3443; Liu et al. (1987) *J Immunol.* 139:3521–3526; Sun et al. (1987) *PNAS* 84:214–218; Nishimura et al. (1987) *Cancer Res* 47:999–1005; Wood et al. (1985) *Nature* 314:446–449; Shaw et al. (1988) *J Natl Cancer Inst* 80:1553–1559); Morrison(1985) *Science* 229:1202–1207; Oi et al. (1986) *BioTechniques* 4:214; U.S. Pat. No. 5,225,539; Jones et al. (1986) *Nature* 321:552–525; Verhoeyan et al. (1988) *Science* 239:1534; and Beidler et al. (1988) *J Immunol* 141:4053–4060.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a OPGx protein is facilitated by generation of hybridomas that bind to the fragment of a OPGx protein possessing such a domain. Antibodies that are specific for a domain within a OPGx protein, or derivatives, fragments, analogs or homologs thereof, are also provided herein.

Anti-OPGx antibodies may be used in methods known within the art relating to the localization and/or quantitation of a OPGx protein (e.g., for use in measuring levels of the OPGx protein within appropriate physiological samples, for use in diagnostic methods, for use in imaging the protein, and the like). In a given embodiment, antibodies for OPGx proteins, or derivatives, fragments, analogs or homologs thereof, that contain the antibody derived binding domain, are utilized as pharmacologically-active compounds [hereinafter "Therapeutics"].

An anti-OPGx antibody (e.g., monoclonal antibody) can be used to isolate OPGx by standard techniques, such as affinity chromatography or immunoprecipitation. An anti-OPGx antibody can facilitate the purification of natural OPGx from cells and of recombinantly produced OPGx expressed in host cells. Moreover, an anti-OPGx antibody can be used to detect OPGx protein (e.g., in a cellular lysate or cell supernatant) in order to evaluate the abundance and pattern of expression of the OPGx protein. Anti-OPGx antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

OPGx Recombinant Expression Vectors and Host Cells

Another aspect of the invention pertains to vectors, preferably expression vectors, containing a nucleic acid encoding OPGx protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence. This can include, e.g., an in vitro transcription/translation system or a host cell when the vector is introduced into the host cell. The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., OPGx proteins, mutant forms of OPGx, fusion proteins, etc.).

The recombinant expression vectors of the invention can be designed for expression of OPGx in prokaryotic or eukaryotic cells. For example, OPGx can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in E. coli is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111–2118). Such alteration of nucleic acid sequences of the invention can be carried out by standard DNA synthesis techniques.

In another embodiment, the OPGx expression vector is a yeast expression vector. Examples of vectors for expression in yeast S. cerivisae include pYepSec1 (Baldari, et al., (1987) EMBO J 6:229–234), pMFa (Kurjan and Herskowitz, (1982) Cell 30:933–943), pJRY88 (Schultz et al., (1987) Gene 54:113–123), pYES2 (Invitrogen Corporation, San Diego, Calif.), and picZ (InVitrogen Corp, San Diego, Calif.).

Alternatively, OPGx can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268–277), lymphoid-specific promoters (Calame and Eaton (1988) Adv Immunol 43:235–275), in particular promoters of T cell receptors (Winoto and Baltimore (1989) EMBO J 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) PNAS 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249:374–379) and the α-fetoprotein promoter (Campes and Tilghman (1989) Genes Dev 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to OPGx mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, OPGx protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding OPGx or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) OPGx protein. Accordingly, the invention further provides methods for producing OPGx protein using the host cells of the invention. In one embodiment, the method comprises culturing the host cell of invention (into which a recombinant expression vector encoding OPGx has been introduced) in a suitable medium such that OPGx protein is produced. In another embodiment, the method further comprises isolating OPGx from the medium or the host cell.

Transgenic Animals

The host cells of the invention can also be used to produce nonhuman transgenic animals. For example, in one embodiment, a host cell of the invention is a fertilized oocyte or an embryonic stem cell into which OPGx-coding sequences have been introduced. Such host cells can then be used to create non-human transgenic animals in which exogenous OPGx sequences have been introduced into their genome or homologous recombinant animals in which endogenous OPGx sequences have been altered. Such animals are useful for studying the function and/or activity of OPGx and for identifying and/or evaluating modulators of OPGx activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous OPGx gene has been altered by homologous recombination between the endogenous gene and an exogenous DNA molecule introduced into a cell of the animal, e.g., an embryonic cell of the animal, prior to development of the animal.

A transgenic animal of the invention can be created by introducing OPGx-encoding nucleic acid into the male pronuclei of a fertilized oocyte, e.g., by microinjection, retroviral infection, and allowing the oocyte to develop in a pseudopregnant female foster animal. The human OPGx DNA sequence of SEQ ID NOs: 2, 4, 6, or 8 can be introduced as a transgene into the genome of a non-human animal. Alternatively, a nonhuman homologue of the human OPGx gene, such as a mouse OPGx gene, can be isolated based on hybridization to the human OPGx cDNA (described further above) and used as a transgene. Intron sequences and polyadenylation signals can also be included in the transgene to increase the efficiency of expression of the transgene. A tissue-specific regulatory sequence(s) can be operably linked to the OPGx transgene to direct expression of OPGx protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the OPGx transgene in its genome and/or expression of OPGx mRNA in tissues or cells of the animals. A transgenic founder animal can then be used to breed additional animals carrying the transgene. Moreover, transgenic animals carrying a transgene encoding OPGx can further be bred to other transgenic animals carrying other transgenes.

To create a homologous recombinant animal, a vector is prepared which contains at least a portion of a OPGx gene into which a deletion, addition or substitution has been introduced to thereby alter, e.g., functionally disrupt, the OPGx gene. The OPGx gene can be a human gene (e.g., the DNA of SEQ ID NOs: 2, 4, 6, or 8, but more preferably, is a non-human homologue of a human OPGx gene. For example, a mouse homologue of a human OPGx gene, e.g., SEQ ID NO:10, can be used to construct a homologous recombination vector suitable for altering an endogenous OPGx gene in the mouse genome. In one embodiment, the vector is designed such that, upon homologous recombination, the endogenous OPGx gene is functionally disrupted (i.e., no longer encodes a functional protein; also referred to as a "knock out" vector).

Alternatively, the vector can be designed such that, upon homologous recombination, the endogenous OPGx gene is mutated or otherwise altered but still encodes functional protein (e.g., the upstream regulatory region can be altered to thereby alter the expression of the endogenous OPGx protein). In the homologous recombination vector, the altered portion of the OPGx gene is flanked at its 5' and 3' ends by additional nucleic acid of the OPGx gene to allow for homologous recombination to occur between the exogenous OPGx gene carried by the vector and an endogenous OPGx gene in an embryonic stem cell. The additional flanking OPGx nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced OPGx gene has homologously recombined with the endogenous OPGx gene are selected (see e.g., Li et al. (1992) *Cell* 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The OPGx nucleic acid molecules, OPGx proteins, and anti-OPGx antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a OPGx protein or anti-OPGx antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, injection, e.g. (see U.S. Pat. Nos. 5,589,466, and 5,580,859), intravenous injection, e.g., local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

The isolated nucleic acid molecules of the invention can be used to express OPGx protein (e.g., via a recombinant expression vector in a host cell in gene therapy applications), to detect OPGx mRNA (e.g., in a biological sample) or a genetic lesion in a OPGx gene, and to modulate OPGx activity, as described further below. In addition, the OPGx proteins can be used to screen drugs or compounds that modulate the OPGx activity or expression as well as to treat disorders characterized by insufficient or excessive production of OPGx protein or production of OPGx protein forms that have decreased or aberrant activity compared to OPGx wild type protein (e.g. proliferative disorders such as cancer or preclampsia. In addition, the anti-OPGx antibodies of the invention can be used to detect and isolate OPGx proteins and modulate OPGx activity.

This invention further pertains to novel agents identified by the above described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) that bind to OPGx proteins or have a stimulatory or inhibitory effect on, for example, OPGx expression or OPGx activity.

In one embodiment, the invention provides assays for screening candidate or test compounds which bind to or modulate the activity of the membrane-bound form of a OPGx protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of OPGx protein, or a biologically active portion thereof, on the cell surface is contacted with a test compound and the ability of the test compound to bind to a OPGx protein determined. The cell, for example, can of mammalian origin or a yeast cell. Determining the ability of the test compound to bind to the OPGx protein can be accomplished, for example, by coupling the test compound with a radioisotope or enzymatic label such that binding of the test compound to the OPGx protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of OPGx protein, or a biologically active portion thereof, on the cell surface with a known compound which binds OPGx to form an assay mixture, contacting the assay mixture with a test compound, and determining the ability of the test compound to interact with a OPGx protein, wherein determining the ability of the test compound to interact with a OPGx protein comprises determining the ability of the test compound to preferentially bind to OPGx or a biologically active portion thereof as compared to the known compound.

In another embodiment, an assay is a cell-based assay comprising contacting a cell expressing a membrane-bound form of OPGx protein, or a biologically active portion thereof, on the cell surface with a test compound and determining the ability of the test compound to modulate (e.g., stimulate or inhibit) the activity of the OPGx protein or biologically active portion thereof. Determining the ability of the test compound to modulate the activity of OPGx or a biologically active portion thereof can be accomplished, for example, by determining the ability of the OPGx protein to bind to or interact with a OPGx target molecule. As used herein, a "target molecule" is a molecule with which a OPGx protein binds or interacts in nature, for example, a molecule on the surface of a cell which expresses a OPGx protein, a molecule on the surface of a second cell, a molecule in the extracellular milieu, a molecule associated with the internal surface of a cell membrane or a cytoplasmic molecule. A OPGx target molecule can be a non-OPGx molecule or a OPGx protein or polypeptide of the present invention. In one embodiment, a OPGx target molecule is a component of a signal transduction pathway that facilitates transduction of an extracellular signal (e.g. a signal generated by binding of a compound to a membrane-bound OPGx molecule) through the cell membrane and into the cell. The target, for example, can be a second intercellular protein that has catalytic activity or a protein that facilitates the association of downstream signaling molecules with OPGx.

Determining the ability of the OPGx protein to bind to or interact with a OPGx target molecule can be accomplished by one of the methods described above for determining direct binding. In one embodiment, determining the ability of the OPGx protein to bind to or interact with a OPGx target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a OPGx-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a OPGx protein or biologically active portion thereof with a test compound and determining the ability of the test compound to bind to the OPGx protein or biologically active portion thereof. Binding of the test compound to the OPGx protein can be determined either directly or indirectly as described above. In one embodiment, the assay comprises contacting the OPGx protein or biologically active portion thereof with a known compound which binds OPGx to form an assay mixture, contacting the assay mixture with a test compound, and determining the ability of the test compound to interact with a OPGx protein, wherein determining the ability of the test compound to interact with a OPGx protein comprises determining the ability of the test compound to preferentially bind to OPGx or biologically active portion thereof as compared to the known compound.

In another embodiment, an assay is a cell-free assay comprising contacting OPGx protein or biologically active portion thereof with a test compound and determining the ability of the test compound to modulate (e.g., stimulate or inhibit) the activity of the OPGx protein or biologically active portion thereof. Determining the ability of the test compound to modulate the activity of OPGx can be accomplished, for example, by determining the ability of the OPGx protein to bind to a OPGx target molecule by one of the methods described above for determining direct binding. In an alternative embodiment, determining the ability of the test compound to modulate the activity of OPGx can be accomplished by determining the ability of the OPGx protein further modulate a OPGx target molecule. For example, the catalytic/enzymatic activity of the target molecule on an appropriate substrate can be determined as previously described.

In yet another embodiment, the cell-free assay includes contacting the OPGx protein or biologically active portion thereof with a known compound which binds OPGx to form an assay mixture. The assay mixture is then contacted with a test compound, and the ability of the test compound to interact with a OPGx protein is determined. Determining the ability of the test compound to interact with a OPGx protein includes determining the ability of the OPGx protein to preferentially bind to or modulate the activity of a OPGx target molecule.

The cell-free assays of the present invention are amenable to use of both soluble forms and membrane-bound forms of OPGx. In the case of cell-free assays comprising the membrane-bound form of OPGx, it may be desirable to utilize a solubilizing agent such that the membrane-bound form of OPGx is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Tritone® X-100, Tritone® X-114, Thesit®, Isotridecypoly(ethylene glycol ether)$_n$, 3-(3-cholamidopropyl)dimethylamminiol-1-propane sulfonate (CHAPS), 3-(3-cholamidopropyl)dimethylamminiol-2-hydroxy-1-propane sulfonate (CHAPSO), or N-dodecyl-N,N-dimethyl-3-ammonio-1-propane sulfonate.

In more than one embodiment of the above assay methods of the present invention, it may be desirable to immobilize either OPGx or its target molecule to facilitate separation of complexed from uncomplexed forms of one or both of the proteins, as well as to accommodate automation of the assay. Binding of a test compound to OPGx, or interaction of OPGx with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-OPGx fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or OPGx protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of OPGx binding or activity determined using standard techniques.

Other techniques for immobilizing proteins on matrices can also be used in the screening assays of the invention. For example, either OPGx or its target molecule can be immobilized utilizing conjugation of biotin and streptavidin. Biotinylated OPGx or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with OPGx or target molecules, but which do not interfere with binding of the OPGx protein to its target molecule, can be derivatized to the wells of the plate, and unbound target or OPGx trapped in the wells by antibody conjugation. Methods for detecting such complexes, in addition to those described above for the GST-immobilized complexes, include immunodetection of complexes using antibodies reactive with the OPGx or target molecule, as well as enzyme-linked assays that rely on detecting an enzymatic activity associated with the OPGx or target molecule.

In another embodiment, modulators of OPGx expression are identified in a method wherein a cell is contacted with a candidate compound and the expression of OPGx mRNA or protein in the cell is determined. The level of expression of OPGx mRNA or protein in the presence of the candidate compound is compared to the level of expression of OPGx mRNA or protein in the absence of the candidate compound. The candidate compound can then be identified as a modulator of OPGx expression based on this comparison. For example, when expression of OPGx mRNA or protein is greater (statistically significantly greater) in the presence of the candidate compound than in its absence, the candidate compound is identified as a stimulator of OPGx mRNA or protein expression. Alternatively, when expression of OPGx mRNA or protein is less (statistically significantly less) in the presence of the candidate compound than in its absence, the candidate compound is identified as an inhibitor of OPGx mRNA or protein expression. The level of OPGx mRNA or protein expression in the cells can be determined by methods described herein for detecting OPGx mRNA or protein.

In yet another aspect of the invention, the OPGx proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), to identify other proteins that bind to or interact with OPGx ("OPGx-binding proteins" or "OPGx-bp") and modulate OPGx activity. Such OPGx-binding proteins are also likely to be involved in the propagation of signals by the OPGx proteins as, for example, upstream or downstream elements of the OPGx pathway.

The two-hybrid system is based on the modular nature of most transcription factors, which consist of separable DNA-binding and activation domains. Briefly, the assay utilizes two different DNA constructs. In one construct, the gene that codes for OPGx is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a OPGx-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with OPGx.

The invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the OPGx, sequences, described herein, can be used to map the location of the OPGx genes, respectively, on a chromosome. The mapping of the OPGx sequences to chromosomes is an important first step in correlating these sequences with genes associated with disease.

Briefly, OPGx genes can be mapped to chromosomes by preparing PCR primers (preferably 15–25 bp in length) from the OPGx sequences. Computer analysis of the OPGx, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the OPGx sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the OPGx sequences to design oligonucleotide primers, sublocalization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see Verma et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, for example, in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, for example, Egeland et al. (1987) Nature, 325:783–787.

Moreover, differences in the DNA sequences between individuals affected and unaffected with a disease associated with the OPGx gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Diagnostic Assays

An exemplary method for detecting the presence or absence of OPGx in a biological sample involves obtaining a biological sample from a test subject and contacting the biological sample with a compound or an agent capable of detecting OPGx protein or nucleic acid (e.g., mRNA, genomic DNA) that encodes OPGx protein such that the presence of OPGx is detected in the biological sample. An agent for detecting OPGx mRNA or genomic DNA is a labeled nucleic acid probe capable of hybridizing to OPGx mRNA or genomic DNA. The nucleic acid probe can be, for example, a full-length OPGx nucleic acid, such as the nucleic acid of SEQ ID NOs: 1, 3, 5, 7, 9, or portions thereof, such as an oligonucleotide of at least 15, 30, 50, 100, 250 or 500 nucleotides in length and sufficient to specifically hybridize under stringent conditions to OPGx mRNA or genomic DNA. Other suitable probes for use in the diagnostic assays of the invention are described herein.

An agent for detecting OPGx protein is an antibody capable of binding to OPGx protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect OPGx mRNA, protein, or genomic DNA in a biological sample in vitro as well as in vivo. For example, in vitro techniques for detection of OPGx mRNA include Northern hybridizations and in situ hybridizations. In vitro techniques for detection of OPGx protein include enzyme linked immunosorbent assays (ELISAs), Western blots, immunoprecipitations and immunofluorescence. In vitro techniques for detection of OPGx genomic DNA include Southern hybridizations. Furthermore, in vivo techniques for detection of OPGx protein include introducing into a subject a labeled anti-OPGx antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting OPGx protein, mRNA, or genomic DNA, such that the presence of OPGx protein, mRNA or genomic DNA is detected in the biological sample, and comparing the presence of OPGx protein, mRNA or genomic DNA in the control sample with the presence of OPGx protein, mRNA or genomic DNA in the test sample.

The invention also encompasses kits for detecting the presence of OPGx in a biological sample. For example, the kit can comprise: a labeled compound or agent capable of detecting OPGx protein or mRNA in a biological sample; means for determining the amount of OPGx in the sample; and means for comparing the amount of OPGx in the sample with a standard. The compound or agent can be packaged in a suitable container. The kit can further comprise instructions for using the kit to detect OPGx protein or nucleic acid.

Prognostic Assays

The diagnostic methods described herein can furthermore be utilized to identify subjects having or at risk of developing a disease or disorder associated with aberrant OPGx expression or activity. For example, the assays described herein, such as the preceding diagnostic assays or the following assays, can be utilized to identify a subject having or at risk of developing a disorder associated with OPGx protein, nucleic acid expression or activity such as bone-metabolism associated disorders, e.g., osteoporosis, disorders characterized by unwanted cell proliferation, or disorders caused by unwanted vascular calcification. Alternatively, the prognostic assays can be utilized to identify a subject having or at risk for developing a disease or disorder. Thus, the present invention provides a method for identifying a disease or disorder associated with aberrant OPGx expression or activity in which a test sample is obtained from a subject and OPGx protein or nucleic acid (e.g., mRNA, genomic DNA) is detected, wherein the presence of OPGx protein or nucleic acid is diagnostic for a subject having or at risk of developing a disease or disorder associated with aberrant OPGx expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant OPGx expression or activity. Thus, the present invention provides methods for determining whether a subject can be effectively treated with an agent for a disorder associated with aberrant OPGx expression or activity in which a test sample is obtained and OPGx protein or nucleic acid is detected (e.g., wherein the presence of OPGx protein or nucleic acid is diagnostic for a subject that can be administered the agent to treat a disorder associated with aberrant OPGx expression or activity.)

The methods of the invention can also be used to detect genetic lesions in a OPGx gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a OPGx-protein, or the mis-expression of the OPGx gene. For example, such genetic lesions can be detected by ascertaining the existence of at least one of (1) a deletion of one or more nucleotides from a OPGx gene; (2) an addition of one or more nucleotides to a OPGx gene; (3) a substitution of one or more nucleotides of a OPGx gene, (4) a chromosomal rearrangement of a OPGx gene; (5) an alteration in the level of a messenger RNA transcript of a OPGx gene, (6) aberrant modification of a OPGx gene, such as of the methylation pattern of the genomic DNA, (7) the presence of a non-wild type splicing pattern of a messenger RNA transcript of a OPGx gene, (8) a non-wild type level of a OPGx-protein, (9) allelic loss of a OPGx gene, and (10) inappropriate post-translational modification of a OPGx-protein. As described herein, there are a large number of assay techniques known in the art which can be used for detecting lesions in a OPGx gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the OPGX-gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to a OPGx gene under conditions such that hybridization and amplification of the OPGx gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sci USA* 86:1173–1177), Q-Beta Replicase (Lizardi et al, 1988, *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a OPGx gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in OPGx can be identified by hybridizing a sample and control nucleic acids, e.g., DNA or RNA, to high density arrays containing hundreds or thousands of oligonucleotides probes (Cronin et al. (1996) *Human Mutation* 7: 244–255; Kozal et al. (1996) *Nature Medicine* 2: 753–759). For example, genetic mutations in OPGx can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the OPGx gene and detect mutations by comparing the sequence of the sample OPGx with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g., PCT International Publ. No. WO 94/16101; Cohen et al. (1996) *Adv Chromatogr* 36:127–162; and Griffin et al. (1993) *Appl Biochem Biotechnol* 38:147–159).

Other methods for detecting mutations in the OPGx gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type OPGx sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in OPGx cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a OPGx sequence, e.g., a wild-type OPGx sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in OPGx genes. For example, single strand conformation polymorphism (SSCP) may be used to detect differences in electrophoretic mobility between mutant and wild type nucleic acids (Orita et al. (1989) *Proc Natl Acad Sci USA:* 86:2766, see also Cotton (1993) *Mutat Res* 285:125–144; Hayashi (1992) *Genet Anal Tech Appl* 9:73–79). Single-stranded DNA fragments of sample and control OPGx nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc Natl Acad Sci USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a OPGx gene.

Furthermore, any cell type or tissue, preferably peripheral blood leukocytes, in which OPGx is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on OPGx activity (e.g., OPGx gene expression), as identified by a screening assay described herein can be administered to individuals to treat (prophylactically or therapeutically) disorders (e.g., cancer or gestational disorders associated with aberrant OPGx activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of OPGx protein, expression of OPGx nucleic acid, or mutation content of OPGx genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, *Clin Exp Pharmacol Physiol*, 1996, 23:983–985 and Linder, *Clin Chem*, 1997, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

The activity of OPGx protein, expression of OPGx nucleic acid, or mutation content of OPGx genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a OPGx modulator, such as a modulator identified by one of the exemplary screening assays described herein.

Monitoring of Effects During Clinical Trials

Monitoring the influence of agents (e.g., drugs, compounds) on the expression or activity of OPGx (e.g., the ability to modulate aberrant cell proliferation and/or differentiation) can be applied not only in basic drug screening, but also in clinical trials. For example, the effectiveness of an agent determined by a screening assay as described herein to increase OPGx gene expression, protein levels, or upregulate OPGx activity, can be monitored in clinical trails of subjects exhibiting decreased OPGx gene expression, protein levels, or downregulated OPGx activity. Alternatively, the effectiveness of an agent determined by a screening assay to decrease OPGx gene expression, protein levels, or downregulate OPGx activity, can be monitored in clinical trails of subjects exhibiting increased OPGx gene expression, protein levels, or upregulated OPGx activity. In such clinical trials, the expression or activity of OPGx and, preferably, other genes that have been implicated in, for example, a cellular proliferation disorder can be used as a "read out" or markers of the immune responsiveness of a particular cell.

For example, and not by way of limitation, genes, including OPGX, that are modulated in cells by treatment with an agent (e.g., compound, drug or small molecule) that modulates OPGx activity (e.g., identified in a screening assay as described herein) can be identified. Thus, to study the effect of agents on cellular proliferation disorders, for example, in a clinical trial, cells can be isolated and RNA prepared and analyzed for the levels of expression of OPGx and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of OPGx or other genes. In this way, the gene expression pattern can serve as a marker, indicative of the physiological response of the cells to the agent. Accordingly, this response state may be determined before, and at various points during, treatment of the individual with the agent.

In one embodiment, the present invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a OPGx protein, mRNA, or genomic DNA in the preadministration sample; (iii) obtaining one or more post-administration samples from the subject; (iv) detecting the level of expression or activity of the OPGx protein, mRNA, or genomic DNA in the post-administration samples; (v) comparing the level of expression or activity of the OPGx protein, mRNA, or genomic DNA in the pre-administration sample with the OPGx protein, mRNA, or genomic DNA in the post administration sample or samples; and (vi) altering the administration of the agent to the subject accordingly. For example, increased administration of the agent may be desirable to increase the expression or activity of OPGx to higher levels than detected, i.e., to increase the effectiveness of the agent. Alternatively, decreased administration of the agent may be desirable to decrease expression or activity of OPGx to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant OPGx expression or activity.

Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an OPGx polypeptide, or analogs, derivatives, fragments or homologs thereof, (ii) antibodies to an OPGx polypeptide; (iii) nucleic acids encoding an OPGx polypeptide; (iv) administration of antisense nucleic acid and nucleic acids that are "dysfunctional" (i.e., due to a heterologous insertion within the coding sequences of coding sequences to an OPGx polypeptide) are utilized to "knockout" endogenous function of an OPGx polypeptide by homologous recombination (see, e.g., Capecchi, 1989. Science 244: 1288–1292); or (v) modulators (i.e., inhibitors, agonists and antagonists, including additional peptide mimetic of the invention or antibodies specific to a peptide of the invention) that alter the interaction between an OPGx polypeptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an OPGx polypeptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an OPGx polypeptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic Methods

In one aspect, the invention provides a method for preventing, in a subject, a disease or condition associated with an aberrant OPGx expression or activity, by administering to the subject an agent that modulates OPGx expression or at least one OPGx activity. Subjects at risk for a disease that is caused or contributed to by aberrant OPGx expression or activity can be identified by, for example, any or a combination of diagnostic or prognostic assays as described herein. Administration of a prophylactic agent can occur prior to the manifestation of symptoms characteristic of the OPGx aberrancy, such that a disease or disorder is prevented or, alternatively, delayed in its progression. Depending on the type of OPGx aberrancy, for example, a OPGx agonist or OPGx antagonist agent can be used for treating the subject. The appropriate agent can be determined based on screening assays described herein. The prophylactic methods of the present invention are further discussed in the following subsections.

Therapeutic Methods

Another aspect of the invention pertains to methods of modulating OPGx expression or activity for therapeutic purposes. As used herein, "a subject suffering from a decrease in bone mass or at risk of undergoing a decrease in bone mass" relates to a subject in which, or in whom, deposition of insoluble calcium salts in bone occurs to an extent insufficient to compensate for the processes of bone remodeling. Bone remodeling includes processes of removal of insoluble calcium salts from bone, and/or the cells involved in forming such insoluble deposits, such as osteoblasts. The subjects in question may develop this pathological condition by a number of mechanisms, including but not limited to, an insufficiency in production of an osteoclastogenesis inhibiting factor such as an osteoprotegerin. Such a subject may experience an osteoclast-mediated bone reabsorption, wherein the subject is suspected of experiencing osteoclast-mediated bone reabsorption or may be at risk of developing osteoclast-mediated bone reabsorption, The modulatory method of the invention involves contacting a cell with an agent that modulates one or more of the activities of OPGx protein activity associated with the cell. An agent that modulates OPGx protein activity can be an agent as described herein, such as a nucleic acid or a protein, a naturally-occurring cognate ligand of a OPGx protein, a peptide, a OPGx peptidomimetic, or other small molecule. In one embodiment, the agent stimulates one or more OPGx protein activity. Examples of such stimulatory agents include active OPGx protein and a nucleic acid molecule encoding OPGx that has been introduced into the cell. In another embodiment, the agent inhibits one or more OPGx protein activity. Examples of such inhibitory agents include antisense OPGx nucleic acid molecules and anti-OPGx antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a OPGx protein or nucleic acid molecule. In one embodiment, the method involves administering an agent (e.g., an agent identified by a screening assay described herein), or combination of agents that modulates (e.g., upregulates or downregulates) OPGx expression or activity. In another embodiment, the method involves administering a OPGx protein or nucleic acid molecule as therapy to compensate for reduced or aberrant OPGx expression or activity.

Stimulation of OPGx activity is desirable in situations in which OPGx is abnormally downregulated and/or in which increased OPGx activity is likely to have a beneficial effect. One example of such a situation is where a subject has a disorder characterized by aberrant cell proliferation and/or differentiation (e.g., cancer).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

This invention is further illustrated by the following examples, which should not be construed as limiting. The contents of all references, patents and published patent applications cited throughout this application are hereby incorporated by reference.

EXAMPLES

Example 1

Expression of OPGx Proteins

Cloning of OPGx cDNA for mammalian and insect cell expression. PCR primers to amplify coding region for a human hOPGx were designed. The forward primer was 5'-act gga tc CCC GGT TCA GCC ATG GGG (SEQ ID NO:11), and the reverse primer was 5'-gtc ctc gag TGA GGT TAA GT TAC CTT T GGG (SEQ ID NO:12). PCR was initiated by heating 25 ul Mix 1 (75 pmoles primers, 4 ug adult bone marrow cDNA, 5 umoles dNTPs) and 25 ul Mix 2 [1 unit Fidelity Expand polymerase (Boehringer Mannheim), 5 ul 10×Fidelity Expand Buffer] separately at 96° C. for 20 seconds. Mixes 1 and 2 were then pooled, and the following PCR cycling parameters were used: 96° C., 3 min (1 cycle); 96° C., 30 sec, 55° C.,1 min, 68° C., 2 min (10 cycles); 96° C., 30 sec, 60° C., 1 min, 68° C., 2 min (20 cycles); 72° C., 7 min (1 cycle). After PCR, a single DNA fragment of approximately 0.8 kb was obtained. The DNA fragment was digested with BglII and XhoI restriction enzymes, and cloned into the pcDNA3.1 V5His vector (Invitrogen, Carlsbad, Calif.) or into the pBIgHis vector (CuraGen Corporation). The OPGx insert was verified by DNA sequence analysis. The resulting expression vectors are called pcDNA3.1V5HisOPGx for mammalian kidney 293 cell expression and pBIgHisOPGx for insect cell expression.

Expression of hOPGx in human embryonic kidney 293 cells. The pcDNA3.1V5HisOPGx vector was transfected into 293 cells using the LipofectaminePlus reagent following the manufacturer's instructions (Gibco/BRL). The cell pellet and supernatant were harvested 72 hours after transfection and examined for hOPGx expression by Western blotting (reducing conditions) with an anti-V5 antibody. FIG. 7A shows that hOPGx is expressed as a 50-kDa protein secreted by 293 cells.

Construction of pBIgHis baculo expression vector. To construct the pBIgHis expression vector, oligonucleotide primers were designed to amplify the Fc fragment of the human immunoglobulin heavy chain. The forward primer was 5'-CCG CTC GAG TGA GCC CAA ATC TTG TGA CAA A (SEQ ID NO:13) and the reverse primer was 5'-GCT CTA GAC TTT TAC CCG GGG ACA GGG AG (SEQ ID NO:14). PCR was initiated by heating 25 ul Mix 1 (75 pmoles primers, 4 ug adult testis cDNA, 5 umoles dNTPs) and 25 ul Mix 2 [1 unit Fidelity Expand polymerase (Boehringer Mannheim), 5 ul 10×Fidelity Expand Buffer] separately at 96° C. for 20 seconds. Mixes 1 and 2 were then pooled, and the following PCR cycling parameters were used: 96° C., 3 min (1 cycle); 96° C., 30 sec, 55° C., 1 min, 68° C., 2 min (10 cycles); 96° C., 30 sec, 60° C., 1 min, 68° C., 2 min (20 cycles); 72° C., 7 min (1 cycle). After PCR, a single DNA fragment of approximately 0.75 kb was obtained. The DNA fragment was digested with XhoI and XbaI restriction enzymes and cloned into the pCDNA3.1V5His(B) expression vector (Invitrogen, Carlsbad, Calif.). This vector is named as pCDNA3.1 Ig and contains Fc fragment fused to V5 epitope and 6xHis tag. At the next step a recombinant TEV protease cleavage site was introduced to the N-terminus of the Fc fragment. First, we designed two oligonucleotides 5'-AAT TCT GCA GCG AAA ACC TGT ATT TTC AGG GT (SEQ ID NO:15) and 5'-TCG AAC CCT GAA AAT ACA GGT TTT CGC TGC AG (SEQ ID NO:16). These two oligonucleotides were annealed and purified using 20% polyacrylamide gel and ligated into EcoRI and XhoI digested pCNA3.1 Ig, The resulting plasmid is then cut with PstI and PmeI to release a DNA fragment of approximately 0.9 kb, which is ligated into PstI and SmaI digested pBlueBac4.5 (Invitrogen, Carlsbad, Calif.). The plasmid construct obtained is named as pBIgHis. The Fc fragment was verified by sequence analysis.

Construction and isolation of recombinant baculovirus expressing hOPGx. pBIgHisOPGx plasmid DNA was co-transfected with linearized baculovirus DNA (Bac-N-Blue) into SF9 insect cells using liposome-mediated transfer as described by the manufacturer (Invitrogen). Briefly, transfection mixtures containing 4 ug of pBIgHisOPGx, 0.5 ug of Bac-N-BlueT™ and InsectinPlus™ liposomes were added to 60 mm culture dishes seeded with 2×10$^6$ SF9 cells, and incubated with rocking at 27° C. for 4 hours. Fresh culture medium was added and cultures were further incubated for 4 days. The culture medium was then harvested and recombinant viruses were isolated using standard plaque purification procedures. Recombinant viruses expressing β-galactosidase as a marker were readily distinguished from non-recombinant viruses by visually inspecting agarose overlays for blue plaques. Viral stocks were generated by propagation on SF9 cells and screened for expression of hOPGx protein by SDS-PAGE and Western blot analyses (reducing conditions, anti-V5 antibody). FIG. 7B shows that hOPGx is secreted as a 61-kDa protein.

Affinity Purification of hOPGX-Fc Chimera (hOPGXIg). Suspension cultures of SF9 cells grown in Grace's media containing 5% low IgG fetal calf serum were infected with recombinant hOPGXIg/baculovirus at a multiplicity of infection (MOI) of 0.1. Infected cultures were incubated at 27 C. for 4–5 days and the conditioned medium was harvested by low-speed centrifugation to remove cells and debris. The conditioned medium was filtered through a 0.2 micron low-protein binding membrane and analyzed for hOPGx production by western analysis. The clarified conditioned medium was then loaded directly onto a 1 ml protein A column (HiTap rProtein A, Amersham Pharmacia) at a flow rate of 1 ml/min at room temperature. Using the Akta Explorer™ FPLC (Amersham Pharmacia), unbound proteins were then washed from the column with 10 ml of 20 mM NaPO$_4$ (pH 7.0). Bound hOPGXIg was eluted from the column with 25 mM Citrate (pH 2.8) and rapidly neutralized by collecting 0.5 ml fractions in tubes containing 0.5M Hepes (pH 9.1). Fractions containing hOPGXIg were pooled and dialyzed against phosphate buffered saline (PBS) containing 20% glycerol. Purified protein samples were stored at −20 C. Using this single-step purification procedure we typically recover 3 mg of hOPGXIg protein per liter of conditioned medium with a purity of >95%. FIG. 8 shows SDS-PAGE and silver staining analysis of 250 ng purified OPGx-Ig protein.

Example 2

Mapping of Human OPG-X

Oligonucleotide Design and Synthesis

Primer pairs for PCR amplification of OPG-X were designed using the Primer 3 primer selection software package. Oligonucleotides were synthesized by Integrated DNA Technologies, (Coralville, Iowa).

PCR, Electrophoresis and Imaging Conditions

PCR was carried out using the GeneBridge 4 human radiation hybrid panel (Research Genetics Inc., Huntsville, Ala.) as template. In addition to the 93 hybrids in the mapping panel, hamster and human genomic DNA are used as controls. This set, therefore, conforms to a 384-well format. DNA from the RH cell lines (50 ng) was PCR amplified in 10 μl reactions containing 4.5 pmole of each primer, 40 82 M each dNTP, 10% Rediload (Research Genetics, Inc., Huntsville, Ala.) and 1/3× concentration of Advantage cDNA polymerase mix (Clontech, Inc, Palo Alto, Calif.). PCR was performed using a Tetrad thermocycler in an oil-free system (MJ Research) with the following "touchdown" PCR profile: 3 min denaturing at 94° C. followed by 2 cycles of 30 sec at 94° C., 30 sec at 67° C. and 30 sec at 68° C.; 2 cycles of 30 sec at 94° C., 30 sec at 65° C., and 30 sec at 68° C.; and 31 cycles of 30 sec at 94° C., 30 sec at 67° C.

Samples were electrophoresed on a 3% agarose gel (1×TBE) containing 0.5 μg/ml Ethidium bromide and imaged using the AlphaImager 950 still video system (Alpha Innotech, San Leandro, Calif.). The collective set of scores (0=no amplification; 1=amplification; 2=uncertain) for a single marker is called an RH vector. The OPG-X marker was assayed in duplicate to reduce errors, and a consensus was generated from the duplicate vectors.

Chromosomal placement of a human OPG-X gene was accomplished using the Whitehead Institute/Massachusetts Institute of Technology Center for Genome Research radiation hybrid mapping website.

The sequence was found to maps onto Human chromosome 6 at a LOD score of >17. The exact placement is at 6p11.1, essentially on top of D6S452 and 4.92 centiRay (cR) proximal to D6S459: one cR is the distance between markers at which there is a 1% probability of breakage. Based on the radiation dose used to construct this panel, the distance from D6S459 is calculated to be 0.19 cM or approximately 190 kb.

Example 3

Northern Analysis of Expression of OPG in Various Human Tissues

Materials and Methods

Probe Production. The probes used in the Northern analysis were produced by PCR amplification of an OPG-X gene fragment cloned into pCR2.1 (Invitrogen). The primers used in the amplification bind to the M13 forward and reverse sequencing primer sites in the vector and contain the SP6 and T3 promoters (Primers used to amplify probes from pCR2.1: M13FSP6: 5'-GGA TCC ATT TAG GTG ACA CTA TAG AAG CCC AGT CAC GAC GTT GTA AAA CGA CGG C-3' (SEQ ID NO:17) and M13RT3: 5'-CGG CCG AAT TAC CCT CAC TAA AGG GAC GGA TAA CAA TTT CAC ACA GGA AAC AGC-3' (SEQ ID NO:18). The forward primer (M13FSP6) contains an SP6 promoter on the 5' end and the M13 forward sequencing primer on the 3' end. While the reverse primer (M13RT3) contains the T3 promoter on the 5' end and the M13 reverse sequencing primer on the 3' end.

The probes were amplified using the following protocol. One nanogram of plasmid was combined with M13FSP6 and M13RT3 (0.2 μM) in 1×PCR buffer (Advantage cDNA Polymerase Kit, Clonetech), 200 μM each dNTP, and 0.5 μl of Advantage cDNA polymerase mix (50×; Clonetech). The mixture was subjected to denaturation at 94° C. for 2 minutes and cycled 5 times at 5 seconds 94° C. and 3 minutes 72° C., 5 times at 5 seconds 94° C. and 3 minutes 70° C. and, finally, 15 times at 5 seconds 94° C. and 3 minutes 68° C. Following amplification, the PCR products containing the gene fragment of interest were electrophoresed through a 1% low melt agarose gel and purified using the Qiaex II gel extraction kit (Qiagen).

The RNA probe was transcribed using the Stip-EZ RNA probe synthesis kit (Ambion, Inc.) per the manufacturer's instructions. One hundred nanograms of purified probe was labeled using 25 μCi of $^{33}$P-UTP (3 μM; Amersham) in a synthesis reaction using SP6 RNA polymerase. The choice of polymerase was dependent on which strand was the non-coding strand for this particular probe. Following RNA transcription, 1 μl of DNase I is added to the tube and incubated for 15 minutes at 37° C. The unincorporated nucleotides are removed using ProbeQuant G-50 micro columns (Pharmacia Biotech) per the manufacturers instructions. Finally, the probe is quantitated using a Bioscan QC-4000 per the manufacturers instructions (Bioscan).

Hybridization. RNA probes were hybridized to four commercially available Northern Blots at 65° C. in a Robbins Scientific Model 400 hybridization incubator. The blots were obtained from Clontech Laboratories, Inc., catalog numbers 7756-1, 7760-1, 7759-1, and 7767-1. Briefly, the blots were inserted into 15×300 mm glass tubes and prehybridized at 65° C. in 10 ml of Zip-Hyb (Ambion, Inc.) for 30 minutes. The RNA probe (1.0×10$^6$ dpm/ml) was added to 1.0 ml 65° C. Zip-Hyb and placed in the glass tube with the prehybridized northern. Hybridization of the probe was allowed to proceed for 2 hours. Following hybridization, the buffer was removed and the blots were washed twice for 15 minutes in the glass bottles at 65° C. The first wash was with prewarmed (65° C.) 2×SSC, 0.1% SDS, while the second wash was with prewarmed 0.1×SSC, 0.1% SDS. The blots were removed from the glass tubes, wrapped in Saran Wrap and exposed to phosphor screens overnight (Molecular Dynamics). The phosphor screens were scanned the following day on a Molecular Dynamics Storm 840 at 50 micron resolution.

Example 4

Cloning of Mouse OPG-X

A RACE (Rapid Amplification of cDNA Ends) approach was used to obtain the sequence of the mouse OPG-X gene.

Primers (5'-TTC CAT CAG CCC ACG AAT CTT CTC CAC-3' (SEQ ID NO:19); 5'-CTC CAC AAC ATC ATT GCG TCG GTG CTG-3' (SEQ ID NO:20) were designed based on the initially available partial mouse OPG-X sequence (667 bp, with a stop codon) and used in a nested 5'-RACE reaction with Advantage cDNA Polymerase and mouse brain Marathon-Ready cDNA (Clontech), according to the manufacturer's instructions. The reaction parameters were as follows: the initial denaturation step (94 ° C. for 30 s) was followed by 5 cycles of 94° C. for 5 s and 72° C. for 4 min, then 5 cycles of 94° C. for 5 s and 70° C. for 4 min, and finally 25 cycles of 94° C. for 5 s and 68° C. for 4 min. The RACE products were run on a low melting agarose gel, excised and purified with QIAEX II Gel Extraction Kit (Qiagen). The purified products were ligated overnight in the pCR2.1 vector using the TA Cloning Kit (Invitrogen), as recommended by the manufacturer. The resulting constructs were transformed in One Shot TOP 10F' Ultracomp *E. coli* cells (Invitrogen) using standard procedures for chemical transformation. The transformed cells were plated on LB/Kanamycin/X-Gal/IPTG plates and incubated overnight at 37° C. The resulting individual colonies were inoculated in LB/Kanamycin/Ampicillin medium and incubated overnight at 37° C. One L of the resulting culture was used as a template in a long-distance (LD)-PCR with Advantage cDNA Polymerase and vector primers. The reaction parameters were as follows: the initial denaturation step (96° C. for 5 min) was followed by 26 cycles of 96° C. for 1 min, 57° C. for 1 min and 72° C. for 1 min then a final extension step of 72° C. for 10 min. The resulting PCR products were sequenced with a BigDye Terminator Cycle Sequencing Kit (PE Applied Biosystems), according to the manufacturer's instructions.

Sequence analysis demonstrated that the initial mouse OPG-X sequence was extended with 888 bp in the 5'-direction. New primers (5'-CAT TCT CTG TCC CTT TCT TCC GCA CAC-3' (SEQ ID NO:21); 5'-GAC TGA TAC ATT CCA GGT GGG CAG ATG-3' (SEQ ID NO:22) were designed based on the newly obtained sequence and the cycle of 5'-RACE, product purification, ligation, transformation, LD-PCR and sequencing was repeated. The sequence was further extended in the 5'-direction, resulting in a total sequence (2393 bp) that contained the information, required for the initiation of transgenic experiments. The complete nucleic acid sequence is shown in FIG. 9A, and its encoded polypeptide is shown in FIG. 9B.

Example 5

Effects of OPG-X in Normal Female Mice (MSCR/Cu1)

Normal female ICR mice from Harlan Labs were given single daily ip injections of protein or vehicle for 7 days. On the eighth day, animals were anesthetized with Isoflurane and bled for determination of CBC and clinical chemistry alterations. Tissues and organs (see protocol) were removed and weighed and collected into formalin for histopathologic evaluation. Selected tissues were snap frozen in liquid nitrogen and analyzed for RNA.

Live Phase and Necropsy Results

Administration of OPG-X did not adversely affect body weight over the course of the study. Liver weights were decreased in OPG-X-treated mice.

Statistically significant alterations in clinical chemistries consisted of slight elevation of globulin and slight decreases in phosphorus in OPG-X treated mice. OPG-X-treated mice also had significant elevations in hemoglobin and red cell count.

Tissues from vehicle treated mice were normal. Mice treated with OPGx had a variety of splenic alterations ranging from mild lymphoid hyperplasia with minimal single cell necrosis of lymphocytes to mildly increased extramedullary hematopoiesis. One animal had marked focal submucosal hemorrhage and inflammation in the anterior colon.

The reason for the submucosal hemorrhage in one mouse treated with OPGx is unknown but alterations in blood coagulation would have to be considered as gut hemorrhage is common in animals treated with anticoagulants. The mild lymphoid hyperplasia and single cell splenic necrosis may be a result of the intestinal hemorrhage. Similarly, since this was an inflammatory focus, the marrow granulocytic hyperplasia may simply be a response to the local inflammation. However, animal #2 in this group had mildly increased extramedullary hematopoiesis without any obvious underlying cause. The clinical pathology alterations in the erythrogram could suggest a stimulatory effect of this protein on hematopoiesis.

Equivalents

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

What is claimed is:

1. A purified polypeptide comprising the amino acid sequence of SEQ ID NO:4.

2. The polypeptide of claim 1, wherein said polypeptide binds to an osteoprotegerin ligand.

3. A composition comprising the polypeptide of claim 1 and a pharmaceutically acceptable carrier.

4. The polypeptide of claim 1, wherein said polypeptide has osteoprotegerin activity.

* * * * *